United States Patent
Ogundiwin et al.

(10) Patent No.: US 10,362,742 B2
(45) Date of Patent: Jul. 30, 2019

(54) MELON PLANTS WITH WHITEFLY RESISTANCE

(71) Applicant: NUNHEMS B.V., AB Nunhem (NL)

(72) Inventors: Ebenezer Ogundiwin, Woodland, CA (US); Peter Visser, Gainesville, FL (US); Daniel Bellon Doña, Los Alcazares (ES); Jean Poulos, Aptos, CA (US)

(73) Assignee: NUNHEMS B.V., Nunhem (NL)

( * ) Notice: Subject to any disclaimer, the term of this patent is extended or adjusted under 35 U.S.C. 154(b) by 22 days.

(21) Appl. No.: 15/313,008

(22) PCT Filed: May 20, 2015

(86) PCT No.: PCT/EP2015/061103
§ 371 (c)(1),
(2) Date: Nov. 21, 2016

(87) PCT Pub. No.: WO2015/177206
PCT Pub. Date: Nov. 26, 2015

(65) Prior Publication Data
US 2017/0202168 A1 Jul. 20, 2017

Related U.S. Application Data

(60) Provisional application No. 62/001,784, filed on May 22, 2014.

(30) Foreign Application Priority Data

Jun. 25, 2014 (EP) ..................................... 14173854

(51) Int. Cl.
| | |
|---|---|
| A01H 5/08 | (2018.01) |
| A01H 1/04 | (2006.01) |
| C12Q 1/6895 | (2018.01) |
| C12Q 1/6883 | (2018.01) |
| C12Q 1/6827 | (2018.01) |
| A01H 1/02 | (2006.01) |

(52) U.S. Cl.
CPC ................ A01H 5/08 (2013.01); A01H 1/02 (2013.01); A01H 1/04 (2013.01); C12Q 1/6827 (2013.01); C12Q 1/6883 (2013.01); C12Q 1/6895 (2013.01); *C12Q 2600/13* (2013.01); *C12Q 2600/156* (2013.01)

(58) Field of Classification Search
None
See application file for complete search history.

(56) References Cited

FOREIGN PATENT DOCUMENTS

| EP | 1800535 A1 | 6/2007 |
|---|---|---|
| WO | WO 2014/031770 A2 | 2/2014 |
| WO | WO 2014/090968 A1 | 8/2014 |

OTHER PUBLICATIONS

Boissot et al (2010 Theor. Appl. Genet 121:9-20, provided by Applicant (Year: 2010).*
Boissot et al., "Field Resistance to Bemisia tabaci in Cucumis melo", HortScience 2003, vol. 38, No. 1, pp. 77-80.
Allen et al., "Transcript-specific, single-nucleotide polymorphism discovery and linkage analysis in hexaploid bread wheat", Plant Biotechnology Journal, 2011, J. 9, pp. 1086-1099.
Boissot et al., Mapping and Validation of QTLs for Resistance to Aphids and Whiteflies in Melon, Theoretical and Applied Genetics, 2010, vol. 121:1, pp. 9-20.
Cuevas et al., A consensus Linkage Map Identifies Genomic Regions Controlling Fruit Maturity and Beta-carotene-associated Flesh Color in Melon (*Cucumis melo* L.), Theoretical and Applied Genetics, 2009, vo. 119:4, pp. 741-756.
Deleu et al., A set of EST-SNPs for Map Saturation and Cultivar Identification in Melon, BMC Plant Biology, 2009, vol. 9:90, pp. 1-9.
Diaz et al., "A consensus linkage map for molecular markers and Quantitative Trait Loci associated with economically important traits in melon (*Cucumis melo* L.)," BMC Plant Biology, vol. 11, 2011, pp. 1-14
Eduardo et al., Estimating the Genetic Architecture of Fruit Quality Traits in Melon Using a Genomic Library of Near Isogenic Lines, Journal of the American Society of Horticultural Science, 2007, vol. 132:1, pp. 80-89.
European Search Report issued in European Patent Application No. 14173854 dated Dec. 16, 2014.
Garcia-Mas et al., The genome of melon (*Cucumis melo* L.), PNAS Jul. 17, 2012, vol. 109, No. 29, pp. 1-6.
González et al., "Generation of a BAC-based physical map of the melon genome", BMC Genomics, 2010, vol. 11, No. 339, pp. 1-13.
Henikoff et al., "Amino acid substitution matrices from protein blocks", PNAS 1992, vol. 89, pp. 10915-10919.
International Search Report and Written Opinion issued in International Patent Application No. PCT/EP2015/061103 dated Jul. 27, 2015.
Ji et al., "Ty-3 a begomovirus resistance locus near the Tomato yellow leaf curl virus resistance locus Ty-1 on chromosome 6 of tomato", Mol. Breeding, 2007, vol. 20, pp. 271-284).
Liu, Response of Four Melon Varieties to Silverleaf Whitefly (Homoptera: Aleyrodidae) under Laboratory and Field Conditions, Subtropical Plant Science, 2003, vol. 55, pp. 27-31.
McCreight et al., Silverleaf Whitefly Resistance Strategies in Melon, Cucurbitaceae, 1998, pp. 113-117.
Obando-Ulloa et al., Identification of QTLs Related to Sugar and Organic Acid Composition in Melon Using Near-isogenic Lines, Scientia Horticulturae, 2009, vol. 121:4, pp. 425-433.
Palomares-Rius et al., "Evaluation of non-preference of melon plants by *B. tabaci*," Cucurbit Genetics Cooperative Report, vol. 30, 2007, pp. 23-25.

(Continued)

*Primary Examiner* — Brent T Page
(74) *Attorney, Agent, or Firm* — Arent Fox LLP

(57) ABSTRACT

The present invention relates to the field of melon plants having whitefly resistance, in particular to cultivated melon plants comprising an introgression of a whitefly resistance QTL.

Figure 1:
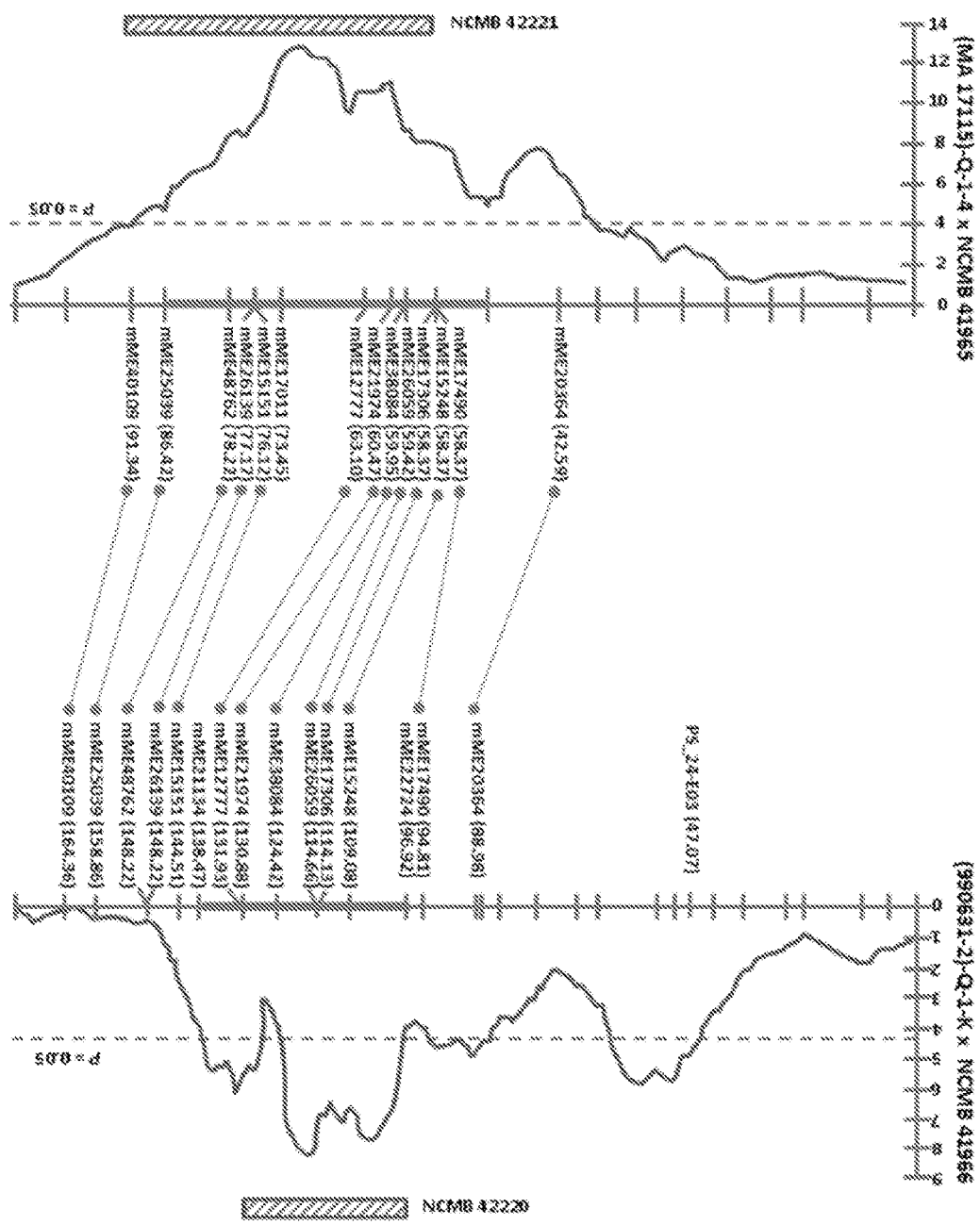

20 Claims, 2 Drawing Sheets
Specification includes a Sequence Listing.

(56) References Cited

OTHER PUBLICATIONS

Sauvion et al., "Impact of Melon Accession Resistant to Aphids on the Demographic Potential of Silverleaf Whitefly," J. Econ. Entomol., vol. 98, 2005, pp. 557-567.
Sebastian et al., "Cucumber (*Cucumis sativus*) and melon (*C. melo*) have numerous wild relatives in Asia and Australia, and the sister species of melon is from Australia", PNAS 2010, vol. 107, No. 32, pp. 14269-14273.
Verlaan et al., "Chromosomal rearrangements between tomato and Solanum chilense hamper mapping and breeding of the TYLCV resistance gene Ty-1", Plant Journal, 2011, vol. 68: pp. 1093-1103.

* cited by examiner

```
                          SEQUENCE LISTING

<160> NUMBER OF SEQ ID NOS: 68

<210> SEQ ID NO 1
<211> LENGTH: 101
<212> TYPE: DNA
<213> ORGANISM: Cucumis melo
<220> FEATURE:
<221> NAME/KEY: variation
<222> LOCATION: (51)..(51)
<223> OTHER INFORMATION: SNP mME20364

<400> SEQUENCE: 1
taagggttgg ttacgcaagg gtcgactttc aatctgtttg agaaaacaag cggttcttag    60
```

```
ctmttgacct ttatgatagg tgccttgaga agggccctcr t                    101
```

<210> SEQ ID NO 2
<211> LENGTH: 85
<212> TYPE: DNA
<213> ORGANISM: Cucumis melo
<220> FEATURE:
<221> NAME/KEY: variation
<222> LOCATION: (35)..(35)
<223> OTHER INFORMATION: SNP mME17490

<400> SEQUENCE: 2

```
gcattttac agcatagaaa aactatggtc gggcaaatta gggatgcaat tacaaagaga    60
aatttgatag agatggaaga tgatt                                         85
```

<210> SEQ ID NO 3
<211> LENGTH: 84
<212> TYPE: DNA
<213> ORGANISM: Cucumis melo
<220> FEATURE:
<221> NAME/KEY: variation
<222> LOCATION: (34)..(34)
<223> OTHER INFORMATION: SNP mME15248

<400> SEQUENCE: 3

```
gtttggtatc tgttgggatc catgattctg catccttact tgtactggaa cttgggagtg   60
tttggaagta ggcagttatt tccc                                          84
```

<210> SEQ ID NO 4
<211> LENGTH: 101
<212> TYPE: DNA
<213> ORGANISM: Cucumis melo
<220> FEATURE:
<221> NAME/KEY: variation
<222> LOCATION: (51)..(51)
<223> OTHER INFORMATION: SNP mME17306

<400> SEQUENCE: 4

```
taatggtgaa aaacaagatt gctgacgata aattggtacc gaattatcaa cacgaaacca   60
aacaaaaact tggctaagtt atgggattgg ataggcattc c                      101
```

<210> SEQ ID NO 5
<211> LENGTH: 101
<212> TYPE: DNA
<213> ORGANISM: Cucumis melo
<220> FEATURE:
<221> NAME/KEY: variation
<222> LOCATION: (51)..(51)
<223> OTHER INFORMATION: SNP mME26059

<400> SEQUENCE: 5

```
acaaaaagta taacacatca atatacgtgg aaacttgtaa agggagaaaa actacgatrg   60
agacttttct tattattttc ttatgaaaca tgaagataca a                      101
```

<210> SEQ ID NO 6
<211> LENGTH: 83
<212> TYPE: DNA
<213> ORGANISM: Cucumis melo
<220> FEATURE:
<221> NAME/KEY: variation
<222> LOCATION: (33)..(33)
<223> OTHER INFORMATION: SNP mME38084

<400> SEQUENCE: 6

```
gccgtgtagc gtctctctct aaaacagaca ttgccataaa atttcagaaa aagaaacaaa   60
```
ttacgaacat aaaaccaaag cat                                                   83

<210> SEQ ID NO 7
<211> LENGTH: 99
<212> TYPE: DNA
<213> ORGANISM: Cucumis melo
<220> FEATURE:
<221> NAME/KEY: variation
<222> LOCATION: (51)..(51)
<223> OTHER INFORMATION: SNP mME21974

<400> SEQUENCE: 7
ttagcggcat gcaaattcac tttatccaaa ggattgattc cgatggtctt cgaggccaga          60
tgcgacattg gcggcgbttg gacrgagacg ctrsacggc                                 99

<210> SEQ ID NO 8
<211> LENGTH: 101
<212> TYPE: DNA
<213> ORGANISM: Cucumis melo
<220> FEATURE:
<221> NAME/KEY: variation
<222> LOCATION: (51)..(51)
<223> OTHER INFORMATION: SNP mME12777

<400> SEQUENCE: 8
tgcggcgaag aatcacacag tctgtaggag tacaataagg attcaaacaa cttagaagga          60
aaatcaatag agcacgattc tatgatactc ctcaaaattg a                             101

<210> SEQ ID NO 9
<211> LENGTH: 101
<212> TYPE: DNA
<213> ORGANISM: Cucumis melo
<220> FEATURE:
<221> NAME/KEY: variation
<222> LOCATION: (51)..(51)
<223> OTHER INFORMATION: SNP mME15151

<400> SEQUENCE: 9
ttctttaaca gttcttgatt cgtgggtctc tttcttttgt tgaatgtaga gcgttcttcc          60
ttgtcattgt ggtagaaaga aagtgaattg aaactttaaa g                             101

<210> SEQ ID NO 10
<211> LENGTH: 101
<212> TYPE: DNA
<213> ORGANISM: Cucumis melo
<220> FEATURE:
<221> NAME/KEY: variation
<222> LOCATION: (51)..(51)
<223> OTHER INFORMATION: SNP mME26139

<400> SEQUENCE: 10
atttaaatgc taataaatat catatataca gaaacaaatg actatgacgt caaattagag          60
tagaaattac ctgcttgata caatatagga cagaactgta a                             101

<210> SEQ ID NO 11
<211> LENGTH: 101
<212> TYPE: DNA
<213> ORGANISM: Cucumis melo
<220> FEATURE:
<221> NAME/KEY: variation
<222> LOCATION: (51)..(51)
<223> OTHER INFORMATION: SNP mME48762

<400> SEQUENCE: 11

-continued

```
tttcgaagca tcgtttacaa gctgttcctg tggttgagct ttccaattct cacgtaattg    60
gtttcattac acaggtactt actactggtt ttaacaaccc c                       101

<210> SEQ ID NO 12
<211> LENGTH: 101
<212> TYPE: DNA
<213> ORGANISM: Cucumis melo
<220> FEATURE:
<221> NAME/KEY: variation
<222> LOCATION: (51)..(51)
<223> OTHER INFORMATION: SNP mME25039

<400> SEQUENCE: 12
gagggaagat agttaaacaa ctcggataat gagagagaaa ccacagaaac catggttctt    60
tcattgcata cttaaactar atcaatttgg accttaggtt t                       101

<210> SEQ ID NO 13
<211> LENGTH: 101
<212> TYPE: DNA
<213> ORGANISM: Cucumis melo
<220> FEATURE:
<221> NAME/KEY: variation
<222> LOCATION: (51)..(51)
<223> OTHER INFORMATION: SNP mME40109

<400> SEQUENCE: 13
ttcattgcaa gagtcaacag atagcggtga agatggacaa gctargaagc ttaaaggtgg    60
ctctaggctt acttctgatg cagccaatat tgatatcatt c                       101

<210> SEQ ID NO 14
<211> LENGTH: 192
<212> TYPE: DNA
<213> ORGANISM: Cucumis melo

<400> SEQUENCE: 14
catcttacaa aatgtatcag aggcatttct aaactttttt aaatgagcaa aagtcttgaa    60
aagcagatca aaaacatgcg gcgaagaatc acacagtctg taggagtaca ataaggattc   120
aaacaactta gaaggaaaat caatagagca cgattctatg atactcctca aaattgattc   180
tgcakgtacg ca                                                      192

<210> SEQ ID NO 15
<211> LENGTH: 1485
<212> TYPE: DNA
<213> ORGANISM: Cucumis melo

<400> SEQUENCE: 15 tttttttct cttctttaac agttcttgat tcgtgggtct ctttcttttg ttgaatgtag     60
aacgttcttc cttgtcattg tggtagaaag aaagtgaatt gaaactttaa agctagttgt   120
ttaattgctc tgttctgcca aatgagacct tgtttcttgc tttggaattg tttatgaatg   180
ccgaaactgw tatcgtaaga attggttttty aatgtcaaga atctatttgg catgtttcgg   240
ttatgctttt cttgaatttt ctagaagttt tcctcttata tgaattcttg taaacaattt   300
tggcttgggg agttataatg ctgaaggata ttctcccttt gtctgtctct tcttgtcact   360
ctgctcaaaa gcaatatgat tatgaacttt tacctttagt tccatggctg taatcgtaat   420
gctttggttt gaattgaact tcaagtcatg atatattgga ttagctttga aatatttgat   480
ggttgtattt gtggcatcca gcatgtctca atatggtaaa aaggttaga gtcattgagt   540 aaccttttcca ttttttgttt ttagttttga taaatatgtc tatttggaaa gtattcgttg   600
```

```
tttgccatat cttgatgttt ctaataactg tactccaatt tggaaatcaa aacaaaatac    660
ttttcttgtt ttgttatgtc aatgtgtaac aatccaaagt tagtatcaag agaatcataa    720
gcaacaaata aaaatgagg aagatatgaa atgagcctaa tttatcatca gtcgaagtac     780
tgaagttgtg tgtatttctt cagttgtata gatgggttgt tgctagaacc acaaagcttt    840
tcttgtttcc tttgcactct cagttgcctg agaaaacccg agaggatatc atagtactaa    900
atgtaggttc tataatatga cgataatcat ttggtttatg ttctgttaca ttactggtta    960
catttaataa aactccagga cgatatagta tttgttggat atatttgcat acctagctat   1020
atattataag atgcagataa ttctttcagc tataattgac tttrttttctc ttgtgattt    1080 aaggatttgc aacaacagca acaatatgaa cggggagctg ccctcaatga gatcgaacac   1140
agccgcaaga tcctacttga caagctcaag gattacaaag gagagtattt ggaagtggta   1200
aaggaagctt ctgccttcgc tggggaggca gtaaagaaca accatgacct catgcttccy   1260
ccatatccaa gtcgctccmc atatcctctt cacctagaca atgaccattt atcaccattc   1320
gtrtctgctc gcaaatctgc ccgtaatggg gtaaccttga gctacatgac aaatgatgcc   1380
aaaagagagt caagcgagtc actaagtacc agcaaagaag cgagcacgaa aaacacaagg   1440
aatggattag gttcactcat agctgcakgt acgccgtcta gactg                   1485

<210> SEQ ID NO 16
<211> LENGTH: 134
<212> TYPE: DNA
<213> ORGANISM: Cucumis melo

<400> SEQUENCE: 16
gtttggtatc tgttgggatc catgattctg catccttact tgtactggaa cttgggagtg     60
tttggaagta ggcagttatt tcccatttgc aatctgttat aagaaggtaa aattataaaa    120
gttctttcaa tttt                                                      134

<210> SEQ ID NO 17
<211> LENGTH: 1871
<212> TYPE: DNA
<213> ORGANISM: Cucumis melo

<400> SEQUENCE: 17
gctacacggc tgcaacaaga aaatgagagg gccaattact tagattttc agttgttagt       60 tttgaacatt tcgtttgcat aaatcaaaaa gtctcttaca tgtctccact tatggccaag    120
aaactcattc acagctattc cattttgtgc atacatcatt ggagaggtcc agtagcccca    180
aatccaccaa ggatgcacat catctaaaca taaagagaag ttctcatttt aagtaatttt    240
tcttatgtaa tggtattgaa acacatagg tcacttgaat caaacctcga gctaagacaa     300
atccacccaa acaagaact gtaagtaaag caaatgatcc aaatgtattt gcaacgatga     360
tattccgtcc caatgctcca atcaaacgga acagcgcaga tgccatttgg ttcacacaca    420
ggagcaggag aaaatgtttg aagaatctgc aagtccatca tacgacctaa tgttatcaag    480
aaggtaaaat aatcaaattg gtagttcagt gttagtgttc ttcattttct tgtaccttcc    540
ggcgtttgga tcgaatccaa cgacatagta agtcattacc acccaaattc caacttcgac    600
aaaagtaata gggatcttaa ggatccatgt gggtatagaa tatgcccaag ggggaaagaa    660
gaggaagtcc ctttgcttgt agaacacagg aagtttcaag attgtcaaag caagctcaga    720 gaaccattg aacatgatta tgataatcgc aaagaacaat gctcccatgt aaaccgatcc     780
```

```
atcatctact gtcctccggc gcatctcggt tcggaaaaac aaggtcattg tcacaaaagc    840
catcagaatg agctgaaaaa tgaagaaaca tagtagtgtc aaacatgagc tatcggagag    900
tgaataaaga tatgaactac ggaactaaaa ctcacttgag tcaacttgaa aatgtacaca    960
aatgagtttc tcttcatgag taaaagctcc cttgaaatgc aagctttcaa cagttccttc   1020
ttgctagcac catacttctc ggttgttaaa gcagcagggt ggcttttaga yttgtcaaat   1080
ggagtggcaa gctcatcacc tagcttcttc cccacatgaa atgattgaaa ggcttcagaa   1140
aactcctcca cactgacaaa tctataaacc tcatctctct tagtccaata ttgttcttga   1200
tctttccttg aagtgaccta taaacagtt tccatcagcc aaacaaaatg gatgaaasaa    1260
atagcagaaa agaacacatt atgaaaatgg ggaaagttaa aaggccaaac gagcttactt   1320
cttgtaagaa gtcagctact cctttcctct gagggcaagt gaagcccata tgttggaaga   1380
actcgagcac gttttcacgt ggaccttgat acacaacttg tccatctgat atcagaatta   1440
tgtcatcaaa caattcataa gtttcagggg mcggwtgaag aagagagatc agagcagttc   1500
cattcagaat atgaatggac tgtctcattg aattaacaat ctgatacgtt gtcgaactgt   1560
ccaatcctgt cgatatctcg tccatgaaca gagctctcgc tggtccaacc aacatctccc   1620
cagtcgtcac cctcttcttt tgcccaccgg agatccctcg aaacatttca tctcctacca   1680
ttgtgtcagc acrgatttca agtcctagaa tctgcataaa caatcaaaaa aacattataa   1740
gaccatatac tattagtttm tttgctgctt agttttttg ctgcttagtt attattacaa    1800
aaagttttca cctttagtac ataatctgtc actacattgg tttcttgtcc tcctaaagct   1860
gcakgtacgc a                                                        1871

<210> SEQ ID NO 18
<211> LENGTH: 201
<212> TYPE: DNA
<213> ORGANISM: Cucumis melo

<400> SEQUENCE: 18
tcctaaggta atctgagaga cgttcaattt cagactgttc aaaggatccc taatggtgaa     60
aaacaagatt gctgacgata aattggtacc gaattatcaa cacgaaacca aacaaaaact    120
tggctaagtt atgggattgg ataggcattc cgcttttgac ttttctatca ttggattgaa    180
ctcgaaggaa atgcctcgat c                                              201

<210> SEQ ID NO 19
<211> LENGTH: 190
<212> TYPE: DNA
<213> ORGANISM: Cucumis melo

<400> SEQUENCE: 19
gcatttttac agcatagaaa aactatggtc gggcaaatta gggatgcaat tacaaagaga     60
aatttgatag agatggaaga tgattagatt acctggatga gagttagggc tcctagtaca    120
agaaaggtac ataaaatgaa tgacgccgtc ttagccattt cgccskgtag cttctctata    180
gagacgctac                                                           190

<210> SEQ ID NO 20
<211> LENGTH: 1052
<212> TYPE: DNA
<213> ORGANISM: Cucusmis melo

<400> SEQUENCE: 20
gcgtacmtgc agcggatgta ctttgaagat ccatatccat tatcatcaga tgatcgtaag     60
```

```
ggttggttac gcaagggtcg actttcaatc tgtttgagaa acaagcggt tcttagctmt      120 tgacctttat gataggtgcc ttgagaaggg ccctcrtggt cattgggcaa aaataaatac    180
ctttgttagg ttgatttggc gaagagcaaa aactgcaagt gccttgaaga gaattcccgg    240
accctcctct agtgagaaaa ctatacttgt ctgaaaagga agcgagcata ttacatacaa    300
caaygtactt attctaagca ccatatacat gaatgcaaag aattagaagg aagagactc     360 ttttcctcct aaaaawacga aaggctaacc ttgaatggcc tatcaatgcc tggaattatg    420
ggttctctcg ctagcattag aaatcgagtt acattgtcag agtcatccta atagaagaaa    480
agaaaattgg taatcggtgc agcattagaa tgtatgggct agtaaatcat aattaaatgc    540
ttaagtaaac acctgaatat cttcagcaag tatattcaag ccatatatgg acgcagccac    600
sgagctagca acagctcctg catctttcaa tttgtgaaaa gcaacatgct gcacaatatc    660
maaagtctca tcaactatca ttctgaacca gcaatcaaaa tgatgaaaat tggatgata     720 cgaatatata atcatcaatc atcaaaactt catataagca ttgctgataa ataagcatca    780
acaaaaatct gatttgcctt ctcagaatca ctatygagcc attataataa taaraaatga    840
caagttttcc tgtagaatag accaaaaaat gacaaaatat cataacagta acggagcagc    900
aattgaacag ccaaagataa agtacctttg cagcaccagc agtatcgtcc actgcttctc    960
tcaccaatcc tagccctgtc aatgtgtttt cacactgrgc magagcctga acaagaatca   1020
tgttaagccg kgtagcgtct cagactgcgt ac                                 1052

<210> SEQ ID NO 21
<211> LENGTH: 134
<212> TYPE: DNA
<213> ORGANISM: Cucumis melo

<400> SEQUENCE: 21
ttcaaaagta gaaacaagag aattcaactt gtttcataaa catattccag attttccaca     60
acaacaaata aacctaataa tgaacacaat cgaattcagg cacagaacaa aggccacgat    120
cggagttaaa aaaa                                                      134

<210> SEQ ID NO 22
<211> LENGTH: 124
<212> TYPE: DNA
<213> ORGANISM: Cucumis melo

<400> SEQUENCE: 22
agagacgcta cmcggagtaa gcggattagc ggcatgcaaa ttcactttat ccaaaggatt     60
gattccgatg gtcttagagg ccagatgcga cattggcggc gbttggacrg agacgctrsa    120
cggc                                                                 124

<210> SEQ ID NO 23
<211> LENGTH: 406
<212> TYPE: DNA
<213> ORGANISM: Cucumis melo

<400> SEQUENCE: 23
aatttaaatt ttttgtcaaa tatatacatc aatttacacc ctgaacgtag atttcctagc     60
taatcaatcc agaccattta tcaaataatc tatatctaat tttactagat cccattcaaa    120
atcaactcaa aattatctaa ataaaattac tttttcttcaa aaagtcccca agtagcagaa   180
ccaatagaaa acgggaaatt taatgaagtc gtaagttcaa ctttaacaat ttttaaaaca    240
```

```
aaattctaat agattgttta aactgattta cttattaatt tgagattttt gtggatacaa    300
gccgtaaaag ttaaaaaagg ggtataaatg aacttatatt attcaaaatt tatcaaattt    360
attcatagga aatgaagcac caaggaatac cagaaaataa wtgaca                  406
```

```
<210> SEQ ID NO 24
<211> LENGTH: 585
<212> TYPE: DNA
<213> ORGANISM: Cucumis melo

<400> SEQUENCE: 24
cgctacmcgg ttcagggcca agaatataag cccaaattgc attgtaatca acagagctmc    60 tattttaat cattgtggac ycaacttgtg ttaggtgtgt attaagcaat gccttgtcaa     120
gcacatttga aatgacatgc aacccaagga cacgttgacc tggtatctga caccaacgag    180
aagctagagt gaaaattatt gaaagagaca aaaagtataa cacatcaata tacgtggaaa    240
cttgtaaagg gagaaaaact acgatrgaga cttttcttat tattttctta tgaaacatga    300
agatacaaag gcgaagaatt aacaggcaac aaaagcttta caaaaacgg aaagaaacag     360 taggtaaaat aatttacata aatacccttg agctttcaac atacaagaag cccataaatt    420
ctgacagaag gtttaaagag ttcaaaataa caaacttcta gaagatttga aataaatgaa    480
aaaagagcta tttcataacg aataagaaaa ataaggggcc aaaagtggaa aaaaacyaac    540
agtattttat ggttgaaaaa aattgtcact acaatgaagc aacta                   585
```

```
<210> SEQ ID NO 25
<211> LENGTH: 133
<212> TYPE: DNA
<213> ORGANISM: Cucumis melo

<400> SEQUENCE: 25
gccgtgtagc gtctctctct aaaacagaca ttaccataaa atttcagaaa aagaaacaaa    60
ttacgaacat aaaaccaaag cattaagagt agaatcaaat aaatgaagaa tccaatcaca    120
gaaacagcag gaa                                                     133
```

```
<210> SEQ ID NO 26
<211> LENGTH: 201
<212> TYPE: DNA
<213> ORGANISM: Cucumis melo

<400> SEQUENCE: 26
ttattttcct gttggaatga gggatacact ttttcatgtt cttcttatgt tttcgaagca    60
tcgtttacaa gctgttcctg tggttgagct ttccaattct aacgtaattg gtttcattac    120
acaggtactt actactggtt ttaacaaccc cgtcgattac ttttgactaa tcttatggga    180 caacacctt taacatttag g                                              201
```

```
<210> SEQ ID NO 27
<211> LENGTH: 49
<212> TYPE: DNA
<213> ORGANISM: artificial
<220> FEATURE:
<223> OTHER INFORMATION: primer mME12777

<400> SEQUENCE: 27
gaaggtgacc aagttcatgc tgtaggagta caataaggat tcaaacaac              49
```

```
<210> SEQ ID NO 28
<211> LENGTH: 49
```

```
<212> TYPE: DNA
<213> ORGANISM: artificial
<220> FEATURE:
<223> OTHER INFORMATION: primer mME12777

<400> SEQUENCE: 28
gaaggtcgga gtcaacggat tgtaggagta caataaggat tcaaacaat        49

<210> SEQ ID NO 29
<211> LENGTH: 29
<212> TYPE: DNA
<213> ORGANISM: artificial
<220> FEATURE:
<223> OTHER INFORMATION: common primer mME12777

<400> SEQUENCE: 29
ggagtatcat agaatcgtgc tctattgat                              29

<210> SEQ ID NO 30
<211> LENGTH: 44
<212> TYPE: DNA
<213> ORGANISM: artificial
<220> FEATURE:
<223> OTHER INFORMATION: primer mME15151

<400> SEQUENCE: 30
gaaggtgacc aagttcatgc taccacaatg acaaggaaga acgt             44

<210> SEQ ID NO 31
<211> LENGTH: 44
<212> TYPE: DNA
<213> ORGANISM: artificial
<220> FEATURE:
<223> OTHER INFORMATION: primer mME15151

<400> SEQUENCE: 31
gaaggtcgga gtcaacggat taccacaatg acaaggaaga acgc             44

<210> SEQ ID NO 32
<211> LENGTH: 29
<212> TYPE: DNA
<213> ORGANISM: artificial
<220> FEATURE:
<223> OTHER INFORMATION: common primer mME15151

<400> SEQUENCE: 32
tcgtgggtct ctttcttttg ttgaatgta                              29

<210> SEQ ID NO 33
<211> LENGTH: 44
<212> TYPE: DNA
<213> ORGANISM: artificial
<220> FEATURE:
<223> OTHER INFORMATION: primer mME15248

<400> SEQUENCE: 33
gaaggtgacc aagttcatgc tcccaagttc cagtacaagt aagg             44

<210> SEQ ID NO 34
<211> LENGTH: 46
<212> TYPE: DNA
<213> ORGANISM: artificial
<220> FEATURE:
<223> OTHER INFORMATION: primer mME15248

<400> SEQUENCE: 34
```
gaaggtcgga gtcaacggat tctcccaagt tccagtacaa gtaaga       46

<210> SEQ ID NO 35
<211> LENGTH: 27
<212> TYPE: DNA
<213> ORGANISM: artificial
<220> FEATURE:
<223> OTHER INFORMATION: common primer mME15248

<400> SEQUENCE: 35
tatctgttgg gatccatgat tctgcat       27

<210> SEQ ID NO 36
<211> LENGTH: 43
<212> TYPE: DNA
<213> ORGANISM: artificial
<220> FEATURE:
<223> OTHER INFORMATION: primer mME17011

<400> SEQUENCE: 36
gaaggtgacc aagttcatgc ttgtcgaact gtccaatcct gtc       43

<210> SEQ ID NO 37
<211> LENGTH: 45
<212> TYPE: DNA
<213> ORGANISM: artificial
<220> FEATURE:
<223> OTHER INFORMATION: primer mME17011

<400> SEQUENCE: 37
gaaggtcgga gtcaacggat tgttgtcgaa ctgtccaatc ctgtt       45

<210> SEQ ID NO 38
<211> LENGTH: 25
<212> TYPE: DNA
<213> ORGANISM: artificial
<220> FEATURE:
<223> OTHER INFORMATION: common primer mME17011

<400> SEQUENCE: 38
gagagctctg ttcatggacg agata       25

<210> SEQ ID NO 39
<211> LENGTH: 49
<212> TYPE: DNA
<213> ORGANISM: artificial
<220> FEATURE:
<223> OTHER INFORMATION: primer mME17306

<400> SEQUENCE: 39
gaaggtgacc aagttcatgc tgacgataaa ttggtaccga attatcaac       49

<210> SEQ ID NO 40
<211> LENGTH: 49
<212> TYPE: DNA
<213> ORGANISM: artificial
<220> FEATURE:
<223> OTHER INFORMATION: primer mME17306

<400> SEQUENCE: 40
gaaggtcgga gtcaacggat tgacgataaa ttggtaccga attatcaat       49

<210> SEQ ID NO 41
<211> LENGTH: 29
<212> TYPE: DNA
<213> ORGANISM: artificial

<220> FEATURE:
<223> OTHER INFORMATION: common primer mME17306

<400> SEQUENCE: 41
ctatccaatc ccataactta gccaagttt                                29

<210> SEQ ID NO 42
<211> LENGTH: 46
<212> TYPE: DNA
<213> ORGANISM: artificial
<220> FEATURE:
<223> OTHER INFORMATION: primer mME17409

<400> SEQUENCE: 42
gaaggtgacc aagttcatgc tagcatagaa aaactatggt cgggca             46

<210> SEQ ID NO 43
<211> LENGTH: 44
<212> TYPE: DNA
<213> ORGANISM: artificial
<220> FEATURE:
<223> OTHER INFORMATION: primer mME17490

<400> SEQUENCE: 43
gaaggtcgga gtcaacggat tcatagaaaa actatggtcg ggcg               44

<210> SEQ ID NO 44
<211> LENGTH: 30
<212> TYPE: DNA
<213> ORGANISM: artificial
<220> FEATURE:
<223> OTHER INFORMATION: common primer mME17490

<400> SEQUENCE: 44
caaatttctc tttgtaattg catccctaat                               30

<210> SEQ ID NO 45
<211> LENGTH: 49
<212> TYPE: DNA
<213> ORGANISM: artificial
<220> FEATURE:
<223> OTHER INFORMATION: primer mME20364

<400> SEQUENCE: 45
gaaggtgacc aagttcatgc tgactttcaa tctgtttgag aaaacaagc          49

<210> SEQ ID NO 46
<211> LENGTH: 50
<212> TYPE: DNA
<213> ORGANISM: artificial
<220> FEATURE:
<223> OTHER INFORMATION: primer mME20364

<400> SEQUENCE: 46
gaaggtcgga gtcaacggat tcgactttca atctgtttga gaaaacaagt         50

<210> SEQ ID NO 47
<211> LENGTH: 27
<212> TYPE: DNA
<213> ORGANISM: artificial
<220> FEATURE:
<223> OTHER INFORMATION: common primer mME20364

<400> SEQUENCE: 47
ggcacctatc ataaaggtca akagcta                                  27

```
<210> SEQ ID NO 48
<211> LENGTH: 47
<212> TYPE: DNA
<213> ORGANISM: artificial
<220> FEATURE:
<223> OTHER INFORMATION: primer mME21134

<400> SEQUENCE: 48
gaaggtgacc aagttcatgc taataatgaa cacaatcgaa ttcaggc            47

<210> SEQ ID NO 49
<211> LENGTH: 50
<212> TYPE: DNA
<213> ORGANISM: artificial
<220> FEATURE:
<223> OTHER INFORMATION: primer mME21134

<400> SEQUENCE: 49
gaaggtcgga gtcaacggat tcctaataat gaacacaatc gaattcaggt         50

<210> SEQ ID NO 50
<211> LENGTH: 28
<212> TYPE: DNA
<213> ORGANISM: artificial
<220> FEATURE:
<223> OTHER INFORMATION: common primer mME21134

<400> SEQUENCE: 50 tttttaact ccgatcgtgg cctttgtt                                  28

<210> SEQ ID NO 51
<211> LENGTH: 42
<212> TYPE: DNA
<213> ORGANISM: artificial
<220> FEATURE:
<223> OTHER INFORMATION: primer mME21974

<400> SEQUENCE: 51
gaaggtgacc aagttcatgc tccaatgtcg catctggcct ct                 42

<210> SEQ ID NO 52
<211> LENGTH: 42
<212> TYPE: DNA
<213> ORGANISM: artificial
<220> FEATURE:
<223> OTHER INFORMATION: primer mME21974

<400> SEQUENCE: 52
gaaggtcgga gtcaacggat tccaatgtcg catctggcct cg                 42

<210> SEQ ID NO 53
<211> LENGTH: 29
<212> TYPE: DNA
<213> ORGANISM: artificial
<220> FEATURE:
<223> OTHER INFORMATION: common primer mME21974

<400> SEQUENCE: 53
ttatccaaag gattgattcc gatggtctt                                29

<210> SEQ ID NO 54
<211> LENGTH: 51
<212> TYPE: DNA
<213> ORGANISM: artificial
<220> FEATURE:
<223> OTHER INFORMATION: primer mME22724
```

-continued

<400> SEQUENCE: 54
gaaggtgacc aagttcatgc tgtcaaatat atacatcaat ttacaccctg a          51

<210> SEQ ID NO 55
<211> LENGTH: 49
<212> TYPE: DNA
<213> ORGANISM: artificial
<220> FEATURE:
<223> OTHER INFORMATION: primer mME22724

<400> SEQUENCE: 55
gaaggtcgga gtcaacggat tcaaatatat acatcaattt acaccctgg             49

<210> SEQ ID NO 56
<211> LENGTH: 29
<212> TYPE: DNA
<213> ORGANISM: artificial
<220> FEATURE:
<223> OTHER INFORMATION: common primer mME22724

<400> SEQUENCE: 56
tggtctggat tgattagcta ggaaatcta                                    29

<210> SEQ ID NO 57
<211> LENGTH: 48
<212> TYPE: DNA
<213> ORGANISM: artificial
<220> FEATURE:
<223> OTHER INFORMATION: primer mME26059

<400> SEQUENCE: 57
gaaggtgacc aagttcatgc tacgtggaaa cttgtaaagg gagaaaaa              48

<210> SEQ ID NO 58
<211> LENGTH: 48
<212> TYPE: DNA
<213> ORGANISM: artificial
<220> FEATURE:
<223> OTHER INFORMATION: primer mME26059

<400> SEQUENCE: 58
gaaggtcgga gtcaacggat tacgtggaaa cttgtaaagg gagaaaat              48

<210> SEQ ID NO 59
<211> LENGTH: 30
<212> TYPE: DNA
<213> ORGANISM: artificial
<220> FEATURE:
<223> OTHER INFORMATION: common primer mME26059

<400> SEQUENCE: 59
cgcctttgta tcttcatgtt tcataagaaa                                   30

<210> SEQ ID NO 60
<211> LENGTH: 54
<212> TYPE: DNA
<213> ORGANISM: artificial
<220> FEATURE:
<223> OTHER INFORMATION: primer mME38084

<400> SEQUENCE: 60
gaaggtgacc aagttcatgc tcgtaatttg tttctttttc tgaaatttta tggt       54

<210> SEQ ID NO 61

<211> LENGTH: 53
<212> TYPE: DNA
<213> ORGANISM: artificial
<220> FEATURE:
<223> OTHER INFORMATION: primer mME38084

<400> SEQUENCE: 61
gaaggtcgga gtcaacggat tgtaatttgt ttcttttttct gaaattttat ggc    53

<210> SEQ ID NO 62
<211> LENGTH: 28
<212> TYPE: DNA
<213> ORGANISM: artificial
<220> FEATURE:
<223> OTHER INFORMATION: common primer mME38084

<400> SEQUENCE: 62
tgtagcgtct ctctctaaaa cagacatt    28

<210> SEQ ID NO 63
<211> LENGTH: 49
<212> TYPE: DNA
<213> ORGANISM: artificial
<220> FEATURE:
<223> OTHER INFORMATION: primer mME48762

<400> SEQUENCE: 63
gaaggtgacc aagttcatgc tgtacctgtg taatgaaacc aattacgtt    49

<210> SEQ ID NO 64
<211> LENGTH: 47
<212> TYPE: DNA
<213> ORGANISM: artificial
<220> FEATURE:
<223> OTHER INFORMATION: primer mME48762

<400> SEQUENCE: 64
gaaggtcgga gtcaacggat tacctgtgta atgaaaccaa ttacgtg    47

<210> SEQ ID NO 65
<211> LENGTH: 25
<212> TYPE: DNA
<213> ORGANISM: artificial
<220> FEATURE:
<223> OTHER INFORMATION: common primer mME48762

<400> SEQUENCE: 65
ctgttcctgt ggttgagctt tccaa    25

<210> SEQ ID NO 66
<211> LENGTH: 101
<212> TYPE: DNA
<213> ORGANISM: Cucumis melo
<220> FEATURE:
<221> NAME/KEY: variation
<222> LOCATION: (51)..(51)
<223> OTHER INFORMATION: SNP mME17011

<400> SEQUENCE: 66
tgtctcattg aattaacaat ctgatacgtt gtcgaactgt ccaatcctgt tgatatctcg    60
tccatgaaca gagctctcgc tggtccaacc aacatctccc c    101

<210> SEQ ID NO 67
<211> LENGTH: 94
<212> TYPE: DNA
<213> ORGANISM: Cucumis melo

```
<220> FEATURE:
<221> NAME/KEY: variation
<222> LOCATION: (44)..(44)
<223> OTHER INFORMATION: SNP mME22724

<400> SEQUENCE: 67
aatttaaatt ttttgtcaaa tatatacatc aatttacacc ctgaacgtag atttcctagc      60
taatcaatcc agaccattta tcaaataatc tata                                 94

<210> SEQ ID NO 68
<211> LENGTH: 84
<212> TYPE: DNA
<213> ORGANISM: Cucumis melo
<220> FEATURE:
<221> NAME/KEY: variation
<222> LOCATION: (51)..(51)
<223> OTHER INFORMATION: SNP mME21134

<400> SEQUENCE: 68
attttccaca acaacaaata aacctaataa tgaacacaat cgaattcagg tacagaacaa      60
aggccacgat cggagttaaa aaaa                                            84
```

MELON PLANTS WITH WHITEFLY RESISTANCE

CROSS REFERENCE TO RELATED APPLICATION

This application is a 35 U.S.C. 371 National Phase of PCT Application Number PCT/EP2015/061103 filed May 20, 2015, which claims priority to U.S. provisional application No. 62/001,784 filed May 22, 2014 and European patent application number 14173854.2 filed Jun. 25, 2014. The disclosure of these prior applications are hereby incorporated by reference in their entireties.

FIELD

The present invention relates to the field of plant breeding, in particular melon breeding. The invention provides for the genetic locus conferring silverleaf whitefly (*Bemisia tabaci* biotype B) resistance as found in wild melon accessions or in wild relatives of melon, and cultivated melon plants comprising said genetic locus (or a resistance conferring part thereof), which confers on said plants whitefly resistance. Also provided are seeds from which such plants can be grown, plant parts, cells, tissues or organs of such plants and breeding methods for transferring the white fly resistance locus, or a resistance conferring part thereof, to other cultivated melon plants or plant cells, especially to whitefly susceptible melon plants. Also provided are molecular markers with which said genetic locus can be identified in plants and plant cells and/or transferred into other melon plants or plant cells. As the whitefly resistance present at the genetic locus is dominant, the white fly resistant plants and/or plant cells may comprise the genetic locus in homozygous form or heterozygous form.

BACKGROUND

The silverleaf whitefly, *Bemisia tabaci* (Hemiptera: Aleyrodidae), is an important insect pest of melon and other cucurbit species. Infestation can cause severe yield loss, both directly through feeding damage cause by the whiteflies and larvae, as well as indirectly through sugary excretions serving as substrate for sooty mold and/or transmission of pathogenic viruses, such as CYSDV (Cucurbit Yellow Stunting Disorder), CVYV (Cucurbit Vein Yellowing Virus) or MYaV (Melon Yellowing Associated Virus), and bacteria.

To control *B. tabaci* insecticides, such as imadacloprid, are frequently applied and breeding for resistance is required to reduce insecticide use.

Sauvion et al. (2005, J Econ Entomology 98:557-567) identified three accessions with potential antibiosis resistance to *B. tabaci* biotype B, PI161375, PI414723 and PI532841.

Boissot et al. (2003, HortScience 38(1): 77-80) identified low levels of field resistance in three Indian Accessions (PI414723, PI1164723 and 90625) and one Korean accession (PI1161375).

Boissot et al. (2010; Theor Appl Genet 121: 9-20) mapped QTLs (Quantitative Trait Loci) for *B. tabaci* biotype B resistance, affecting the number of progenies produced by one female of biotype B (antibiosis resistance), to linkage group VII, for one whitefly clonal population, and to linkage group IX, for a different whitefly clonal population. The QTLs were only minor (LOD value 3.6 and 4.0) and the resistance allele for both of these minor QTLs originated from the Korean accession PI161375.

The genetics of whitefly resistance are still largely unknown, most likely to the difficulties to manage whiteflies in the laboratory and difficulties in establishing reliable assays for whitefly resistance.

Tests that are used to identify resistance are either free-choice tests or non-choice tests or field tests.

In free choice assays the insects can choose among different plant genotypes for feeding and reproduction. Such free choice-tests are used to identify antixenosis (non-preference) resistance, i.e. resistance caused by factors that make a plant genotype less attractive. See e.g. Palomares-Rius et al. (2007, Cucurbit Genetics Cooperative Report 30:23-25) who used a free-choice leaf disc assay to show that PI414723 is rejected quickly by whiteflies and that therefore a antixenosis mechanism may exist in this accession in addition to the antibiosis mechanism detected by Sauvion et al. (2005, supra).

In non-choice tests for resistance the insects cannot choose among different plant genotypes for feeding and reproduction, but are only allowed to feed and reproduce on one genotype. This type of resistance affects the insects biotic potential, e.g. they die, produce fewer offspring or grow more slowly (antibiosis or antibiotic resistance).

It is an object of the invention to provide whitefly resistance sources and a genetic region comprising the resistance locus, or a part thereof, which confer resistance, especially antixenosis (non-preference) resistance and field resistance, against whiteflies, *B. tabaci* biotype B. It is a further object of the invention to provide cultivated melon plants (*Cucumis melo* L.) and cells, tissues, fruits and other parts of such plants comprising in their genome a whitefly resistance-conferring locus (or a resistance-conferring part thereof), either in homozygous or heterozygous form, whereby the melon plants are resistant against whitefly. Also seeds from which whitefly resistant melon plants can be grown are an embodiment of the invention.

In a further aspect molecular markers are provided, which can be used to detect the presence of and/or to transfer the *B. tabaci* resistance-conferring locus, or a resistance-conferring part thereof, in/into plants or plant cells of *Cucumis melo* L using e.g. traditional breeding techniques (such as marker assisted selection). One or more of the markers can, thus, for example be used to transfer the resistance locus, or a resistance-conferring part thereof, into cultivated melon plants which are susceptible to *B. tabaci*. In one embodiment the resistance locus, or resistance-conferring part thereof, is the locus on chromosome 11 as found in seeds deposited under accession number NCIMB 41965 or NCIMB 41966. In a different embodiment the resistance locus, or resistance conferring part thereof, is the locus on chromosome 11 as found in seeds deposited under accession number NCIMB 42221 or NCIMB 42220. In a further embodiment the resistance locus or resistance-conferring part thereof is the locus on chromosome 11, or a resistance-conferring part thereof, as found in other wild melon plants or wild relatives of melon.

One or more of the markers linked to, or genetically and physically associated with, the *B. tabaci* resistance locus, or resistance conferring part thereof, can also be used to identify new *B. tabaci*-resistance sources on chromosome 11, such as other wild accessions of *Cucumis melo* or wild relatives of melon comprising a *B. tabaci*-resistance locus on chromosome 11 and for transferring (introgressing) the resistance locus, or a *B. tabaci*-resistance conferring part thereof, from such accessions into cultivated melon plants. The *B. tabaci* resistance conferring quantitative trait locus (QTL) on chromosome 11 (equivalent to ICuGI Linkage Group XI, or LG XI) was named Wf_11.1 (for whitefly chromosome 11, QTL 1).

WO2014/031770 describes a QTL for ZYMV/WMV resistance introgressed onto chromosome 11, but this QTL maps to a different region of chromosome 11, especially to the other half of chromosome 11 than the QTL of the instant invention.

General Definitions

The indefinite article "a" or "an" does not exclude the possibility that more than one of the element is present, unless the context clearly requires that there be one and only one of the elements. The indefinite article "a" or "an" thus usually means "at least one".

As used herein, the term "plant" includes the whole plant or any parts or derivatives thereof, such as plant organs (e.g., harvested or non-harvested storage organs, tubers, fruits, leaves, seeds, etc.), plant cells, plant protoplasts, plant cell or tissue cultures from which whole plants can be regenerated, plant calli, plant cell clumps, and plant cells that are intact in plants, or parts of plants, such as embryos, pollen, ovules, ovaries, fruits (e.g., harvested tissues or organs, such as harvested melon fruits or parts thereof), flowers, leaves, seeds, tubers, bulbs, clonally propagated plants, roots, rootstocks, stems, root tips and the like. Also any developmental stage is included, such as seedlings, immature and mature, etc. When "seeds of a plant" are referred to, these either refer to seeds from which the plant can be grown or to seeds produced on the plant, after self-fertilization or cross-fertilization.

"Plant variety" is a group of plants within the same botanical taxon of the lowest grade known, which (irrespective of whether the conditions for the recognition of plant breeder's rights are fulfilled or not) can be defined on the basis of the expression of characteristics that result from a certain genotype or a combination of genotypes, can be distinguished from any other group of plants by the expression of at least one of those characteristics, and can be regarded as an entity, because it can be multiplied without any change. Therefore, the term "plant variety" cannot be used to denote a group of plants, even if they are of the same kind, if they are all characterized by the presence of one or two loci or genes (or phenotypic characteristics due to these specific loci or genes), but which can otherwise differ from one another enormously as regards the other loci or genes.

"F1, F2, F3, etc." refers to the consecutive related generations following a cross between two parent plants or parent lines. The plants grown from the seeds produced by crossing two plants or lines is called the F1 generation. Selfing the F1 plants results in the F2 generation, etc.

"F1 hybrid" plant (or F1 hybrid seed) is the generation obtained from crossing two inbred parent lines. Thus, F1 hybrid seeds are seeds from which F1 hybrid plants grow. F1 hybrids are more vigorous and higher yielding, due to heterosis.

The term "allele(s)" means any of one or more alternative forms of a gene at a particular locus, all of which alleles relate to one trait or characteristic at a specific locus. In a diploid cell of an organism, alleles of a given gene are located at a specific location, or locus (loci plural) on a chromosome. One allele is present on each chromosome of the pair of homologous chromosomes. A diploid plant species may comprise a large number of different alleles at a particular locus. These may be identical alleles of the gene (homozygous) or two different alleles (heterozygous). Thus, for example reference may herein be made to a Wf-allele of the B. tabaci resistance locus Wf_11.1.

The term "gene" means a (genomic) DNA sequence comprising a region (transcribed region), which is transcribed into a messenger RNA molecule (mRNA) in a cell, and an operably linked regulatory region (e.g. a promoter). Different alleles of a gene are thus different alternatives form of the gene, which may be in the form of e.g. differences in one or more nucleotides of the genomic DNA sequence (e.g. in the promoter sequence, the exon sequences, intron sequences, etc.), mRNA and/or amino acid sequence of the encoded protein.

The term "locus" (loci plural) means a specific place or places or a site on a chromosome where for example a gene or genetic marker is found. The B. tabaci resistance locus or Wf-resistance locus (or B. tabaci resistance-conferring locus) is, thus, the location in the genome of melon, where the Wf-resistance gene is found. In cultivated melon the B. tabaci resistance locus is found on chromosome 11 (using the ICuGI nomenclature for chromosome or Linkage Groups, i.e. LG XI) and is preferably introgressed into the cultivated melon genome (i.e. onto chromosome 11, or LG XI) from wild melon accessions, such as (but not limited to) the two wild melon accessions deposited under accession numbers NCIMB 41965 and NCIMB41966, or from other wild melons or wild relatives of melon which are crossable with C. melo and from which crosses fertile offspring can be produced.

A "quantitative trait locus", or "QTL" is a chromosomal locus that encodes for one or more alleles that affect the expressivity of a continuously distributed (quantitative) phenotype. The B. tabaci resistance conferring quantitative trait locus is named herein Wf_11.1.

"ICuGI" refers to the International Cucurbit Genomics Initiative, which publishes genetic maps of e.g. Cucumis melo (world wide web of icugi.org under cgi-bin/cmap/map_set_info?species_acc=CM). The current version of the C. melo genome map is of Mar. 4, 2012 and the map of chromosome 11 is referred to as ICuGI_XI (or LG XI, or Linkage Group XI) and contains 148 markers (7 AFLP, 3 ISSR, 15 RAPD, 30 RFLP, 29 SNP, 64 SSR markers) on a linkage group spanning 0.00 to 80.00 cM. Herein melon chromosome 11 and LG XI are used interchangeably.

"Genetic distance" between loci (e.g. between molecular markers and/or between phenotypic markers) on the same chromosome is measured by frequency of crossing-over, or recombination frequency (RF) and is indicated in centimorgans (cM). One cM corresponds to a recombination frequency of 1%. If no recombinants can be found, the RF is zero and the loci are either extremely close together physically or they are identical. The further apart two loci are, the higher the RF.

"Physical distance" between loci (e.g. between molecular markers and/or between phenotypic markers) on the same chromosome is the actually physical distance expressed in base pairs (bp), kilo base pairs (kb) or megabase pairs (Mb). C. melo has a total haploid genome size of about 450 Mb, divided into 12 chromosome pairs, see Garcia-Mas et al, PNAS Jul. 2, 2012, p 1-6 and Gonzales et al. 2010, BMC Genomics 11:339, p 1-13.

"Introgression fragment" or "introgression segment" or "introgression region" refers to a chromosome fragment (or chromosome part or region) which has been introduced into another plant of the same or related species by crossing or traditional breeding techniques, such as backcrossing, i.e. the introgressed fragment is the result of breeding methods referred to by the verb "to introgress" (such as backcrossing). In melon, wild melon accessions or wild relatives of melon are often used to introgress fragments of the wild genome into the genome of cultivated melon, *Cucumis melo*. Such a cultivated melon plant thus has a "genome of cultivated *C. melo*", but comprises in the genome a fragment of a wild melon or of a wild relative of melon, e.g. an introgression fragment of a related wild *Cucumis* genome, such as *Cucumis melo* ssp. *agrestis*, *C. melo* ssp. *melo*, *C. melo* ssp. *acidulous*, *C. callosus*, *C. trigonus*, *C. picrocarpus*, or another wild melon or wild relative of melon. It is understood that the term "introgression fragment" never includes a whole chromosome, but only a part of a chromosome. The introgression fragment can be large, e.g. even half of a chromosome, but is preferably smaller, such as about 35 Mb, 34 Mb, 33 Mb, 25 Mb, 20 Mb, 15 Mb or less, such as about 10 Mb or less, about 9 Mb or less, about 8 Mb or less, about 7 Mb or less, about 6 Mb or less, about 5 Mb or less, about 4 Mb or less, about 3 Mb or less, about 2 Mb or less, about 1 Mb (equals 1,000,000 base pairs) or less, or about 0.5 Mb (equals 500,000 base pairs) or less, such as about 200,000 bp (equals 200 kilo base pairs) or less, about 100,000 bp (100 kb) or less, about 50,000 bp (50 kb) or less, about 25,000 bp (25 kb) or less.

A genetic element, an introgression fragment or a gene or allele conferring a trait (such as resistance against whitefly) is said to be "obtainable from" or can be "obtained from" or "derivable from" or can be "derived from" or "as present in" or "as found in" a plant or seed or tissue or cell if it can be transferred from the plant or seed in which it is present into another plant or seed in which it is not present (such as a line or variety) using traditional breeding techniques without resulting in a phenotypic change of the recipient plant apart from the addition of the trait conferred by the genetic element, locus, introgression fragment, gene or allele. The terms are used interchangeably and the genetic element, locus, introgression fragment, gene or allele can thus be transferred into any other genetic background lacking the trait. Not only seeds deposited and comprising the genetic element, locus, introgression fragment, gene or allele can be used, but also progeny/descendants from such seeds which have been selected to retain the genetic element, locus, introgression fragment, gene or allele, can be used and are encompassed herein, such as commercial varieties developed from the deposited seeds or from descendants thereof. Whether a plant (or genomic DNA, cell or tissue of a plant) comprises the same genetic element, locus, introgression fragment, gene or allele as obtainable from the deposited seeds can be determined by the skilled person using one or more techniques known in the art, such as phenotypic assays, whole genome sequencing, molecular marker analysis, trait mapping, chromosome painting, allelism tests and the like.

The "Wf_11.1-allele" or "Wf-allele" or "whitefly resistance allele" refers to a *B. tabaci* biotype B resistance-conferring allele found at the *B. tabaci* resistance-conferring locus Wf_11.1, or at the resistance-conferring part of the locus, introgressed into cultivated melon (onto cultivated *C. melo* chromosome 11) from a wild melon or wild relative of melon, e.g. from plants of which a representative sample of seeds were deposited under accession number NCIMB 41965 or NCIMB 41966. The term "Wf-allele", thus, also encompasses Wf-alleles obtainable from other *B. tabaci* biotype B resistant *Cucumis* accessions, such as Wf_11.1 orthologous alleles (see below). When one or two Wf-alleles are present at the Wf_11.1 resistance-conferring locus in the genome (i.e. in heterozygous or homozygous form), the plant is resistant against *B. tabaci* biotype B, i.e. has a *B. tabaci* resistance phenotype. In cultivated melon plant lacking the introgression fragment, the *C. melo* allele found at the same locus on chromosome 11 is herein referred to as "wf" allele (or whitefly-susceptible allele). As the resistance is dominant, wf/wf plants show a *B. tabaci*-susceptible phenotype, whereas Wf/wf plants and Wf/Wf plants are plants which possess the *B. tabaci* resistant phenotype conferred by the Wf-allele (i.e. are resistant to *B. tabaci* biotype B).

"Wf orthologous alleles" or "Wf orthologs" or "orthologs of Wf" are alleles of Wf_11.1 resistance gene present in other wild relatives of melon, on the orthologous chromosomes 11. Such orthologous alleles may, thus, be found on orthologous chromosome 11 of wild relatives of *C. melo*, such as *C. callosus*, *C. trigonus*, *C. picrocarpus* and others and are transferrable, by introgression, onto cultivated *C. melo* chromosome 11.

A "*B. tabaci* resistance phenotype" or "*B. tabaci* biotype B resistance phenotype" or "Wf resistance" or "whitefly resistance" or "whitefly resistant plants" or "*B. tabaci* biotype B resistant plants" refers to resistance against *B. tabaci* biotype B conferred by the Wf allele (or by the Wf orthologous allele) when present in the *C. melo* genome in one or two copies (i.e. in heterozygous or homozygous from). The Wf resistance phenotype and the presence of the Wf allele and/or orthologs of Wf can be tested using the "Wf resistance assay" and/or the Wf marker assays.

A "Wf-resistance assay" or "Wf assay" can be carried out in different ways, either by controlled environment tests and/or as a field test, as described herein below and in the Examples. The assay is preferably a free-choice assay, preferably in a field with natural whitefly infestation. Sufficient plants per replicate and sufficient replicates should be used, as well as appropriate control plants (especially whitefly susceptible controls, such as varieties Medellin F1 (Nunhems) or Caribbean Gold F1 (Rijk Zwaan), and preferably also resistant controls, such as plants grown from seeds of NCIMB 41965 and NCIMB 41966). Average numbers of adult whiteflies and/or third instar nymphs can be counted on leaf discs and/or on whole leaves in order to determine whether a plant line has whitefly resistance, i.e. statistically the average number of adult whiteflies and/or third instar nymphs is significantly reduced in a whitefly resistant plant line compared to the susceptible control plant.

The "Wf-marker assay" is a molecular marker assay which can be used to test whether on *C. melo* chromosome 11 an introgression from a wild melon, or wild relative of melon, comprising the Wf-resistance allele is present in the genome (or whether in wild melon or wild relatives of melon comprise the Wf_11.1 QTL-comprising region in their genome), by determining the genotype of one or more (e.g. of any 2, 3, 4, 5, 6, 7, 8, 9, 10, 11, 12, 13, 14, 15, 16, or more) SNP (Single Nucleotide Polymorphism) markers of the group consisting of: mME20364 and/or mME17490 and/or mME15248 and/or mME17306 and/or mME26059 and/or mME38084 and/or mME21974 and/or mME12777 and/or mME15151 and/or mME26139 and/or mME48762 and/or mME25039 and/or mME40109 and/or of any wild melon or wild-relative of melon genome-specific marker in-between SNP markers mME20364 and mME40109, such as in between any two of the aforementioned markers as described elsewhere herein and as can be seen on FIG. 1. The molecular markers are genetically and physically linked to Wf_11.1.

"Melon" or "muskmelon" refers herein to plants of the species *Cucumis melo*. Melons or 'muskmelons', *Cucumis melo*, can be classified into: *C. melo cantalupensis*, *C. melo*

*inodorous* and *C. melo reticulatus*. *C. melo cantalupensis* are also referred to as Cantaloupes and are primarily round in shape with prominent ribs and almost no netting. Most have orange, sweet flesh and they are usually very fragrant. In contrast to the European cantaloupe, the North American 'Cantaloupe' is not of this type, but belongs to the true muskmelons. *C. melo inodorous* (or winter melons) can be subdivided into different types, such as Honeydew melon, Piel de Sapo, Sugar melon, Japanese melon, etc. *C. melo reticulatus* is the true muskmelon, with reticulated skin (netted) and includes Galia melons, Sharlyn melons and the North American cantaloupe.

"Cultivated melon" refers to plants of *Cucumis melo* i.e. varieties, breeding lines or cultivars of the species *C. melo*, cultivated by humans and having good agronomic characteristics, especially producing edible and marketable fruits of good size and quality and uniformity; preferably such plants are not "wild plants", i.e. plants which generally have much poorer yields and poorer agronomic characteristics than cultivated plants and e.g. grow naturally in wild populations. "Wild plants" include for example ecotypes, PI (Plant Introduction) lines, landraces or wild accessions or wild relatives of a species.

Melon and the wild relatives of melon is/are diploid and has/have 12 pairs of homologous chromosomes, numbered 1 to 12. "Melon chromosome 11" refers to the *C. melo* chromosome 11, as known in the art and as referred to by the ICuGI nomenclature. "Orthologous chromosome 11" refers to the chromosome 11 of wild relatives of melon, parts of which can be introgressed into cultivated melon chromosome 11.

"Wild melon" includes wild plants of the species *Cucumis melo*, e.g. *C. melo* ssp *agrestis*, *C. melo* ssp. *melo*, *C. melo* var. *texanus*, *C. melo* var. *acidulous*, seeds deposited under NCIMB 41965, NCIMB 41966, and other wild *C. melo* accessions, as e.g. landraces or PI accessions found on http://www.ars-grin.gov or other seed collections. Seeds deposited under NCIMB 41966 were obtained from the ARS-GRIN collection and have as designated origin 'India'. Seeds deposited under NCIMB 41965 were obtained from the ARS-GRIN collection and have an unknown origin.

"Wild relatives of melon" include wild plants of other *Cucumis* species, but which can be crossed with *Cucumis melo* to produce fertile offspring (optionally with the aid of embryo rescue, temperature-dependent enhancement of pollen-tube growth, or similar techniques to overcome reproductive barriers) and from which chromosome fragments can be obtained and transferred into *Cucumis melo* (either by interspecific crosses with *C. melo* or via crosses with a bridge species). Examples of wild relatives of melon are *C. anguria, C. metuliferus, Cucumis callosus, Cucumis trigonus, Cucumis ficifolius, C. picocarpus, C. zeyheri, C. africanus, C. meeusei, C. prophetarum, C. hystrix, C. queenslandicus*, and other *Cucumis* species (see e.g. Sebastian et al. 2010, PNAS Vol 107, no. 32, 14269-14273).

"Average" or "mean" refers herein to the arithmetic mean and both terms are used interchangeably. The term "average" or "mean" thus refers to the arithmetic mean of several measurements. The skilled person understands that the phenotype of a plant line or variety depends to some extent on growing conditions and that, therefore, arithmetic means of at least 10, 15, 20, 30 or more plants (or plant parts) are measured, preferably in randomized experimental designs with several replicates and suitable control plants grown under the same conditions in the same experiment. "Statistically significant" or "statistically significantly different" refers to a characteristic of a plant line or variety (e.g. a cultivated melon plant comprising the Wf_11.1 QTL of the invention) that, when compared to a suitable control (e.g. a Wf susceptible plant line or variety) show a statistically significant difference in that characteristic (e.g. p<0.05 using ANOVA) from the (mean of the) control, e.g. a "statistically significantly reduced" average number of adult whiteflies and/or third instar nymphs in plants comprising the Wf_11.1 QTL compared to susceptible controls.

A "recombinant chromosome" refers to a chromosome having a new genetic makeup arising through crossing over between homologous chromosomes, e.g. a "recombinant chromosome 11", i.e. a chromosome 11 which is not present in either of the parent plants and arose through a rare crossing-over event between homologous chromosomes of a chromosome 11 pair. Herein, for example, a recombinant melon chromosome 11 comprising a Wf-resistance conferring locus, or resistance-conferring part thereof (comprising a Wf-resistance allele), is provided. The recombinant chromosome 11 comprises an introgression fragment from a wild or wild relative of melon, which fragment comprises a Wf-resistance conferring allele (as can be determined through the Wf resistance phenotype and/or by the presence of one or more of the molecular markers).

The term "traditional breeding techniques" encompasses herein crossing, backcrossing, selfing, selection, double haploid production, embryo rescue, protoplast fusion, marker assisted selection (MAS), mutation breeding etc. as known to the breeder (i.e. methods other than genetic modification/transformation/transgenic methods), by which, for example, a recombinant chromosome 11 can be obtained, identified and/or transferred.

"Backcrossing" refers to a breeding method by which a (single) trait, such as Wf resistance, can be transferred from an inferior genetic background (e.g. a wild melon or wild relative of melon; also referred to as "donor") into a superior genetic background (also referred to as "recurrent parent"), e.g. cultivated melon. An offspring of a cross (e.g. an F1 plant obtained by crossing a wild, Wf-resistant melon with a cultivated, Wf-susceptible melon; or an F2 plant or F3 plant, etc., obtained from selfing the F1) is "backcrossed" to the parent with the superior genetic background, e.g. to the cultivated, Wf-susceptible, parent. After repeated backcrossing (BC1, BC2, etc.) and optionally selfings (BC1S1, BC2S1, etc.), the trait of the inferior genetic background is incorporated into the superior genetic background.

"Marker assisted selection" or "MAS" is a process of using the presence of molecular markers, which are genetically linked to a particular locus or to a particular chromosome region (e.g. introgression fragment), to select plants for the presence of the specific locus or region (introgression fragment). For example, a molecular marker genetically and physically linked to an Wf-resistance locus, can be used to detect and/or select melon plants comprising the Wf-resistance locus. The closer the genetic linkage of the molecular marker to the locus (e.g. about 7 cM, 6 cM, 5 cM, 4 cM, 3 cM, 2 cM, 1 cM, 0.5 cM or less), the less likely it is that the marker is dissociated from the locus through meiotic recombination.

"LOD-score" (logarithm (base 10) of odds) refers to a statistical test often used for linkage analysis in animal and plant populations. The LOD score compares the likelihood of obtaining the test data if the two loci (molecular markers loci and/or a phenotypic trait locus) are indeed linked, to the likelihood of observing the same data purely by chance. Positive LOD scores favor the presence of linkage and a LOD score greater than 3.0 is considered evidence for linkage. A LOD score of +3 indicates 1000 to 1 odds that the linkage being observed did not occur by chance.

"Vegetative propagation", "vegetative reproduction" or "clonal propagation" are used interchangeably herein and mean the method of taking part of a plant and allowing that plant part to form at least roots where plant part is, e.g., defined as or derived from (e.g. by cutting of) leaf, pollen, embryo, cotyledon, hypocotyl, cells, protoplasts, meristematic cell, root, root tip, pistil, anther, flower, shoot tip, shoot, stem, fruit, petiole, etc. When a whole plant is regenerated by vegetative propagation, it is also referred to as a vegetative propagation or a vegetatively propagated plant.

"Cell culture" or "tissue culture" refers to the in vitro culture of cells or tissues of a plant.

"Regeneration" refers to the development of a plant from cell culture or tissue culture or vegetative propagation.

"Transgene" or "chimeric gene" refers to a genetic locus comprising a DNA sequence, such as a recombinant gene or a recombinant chromosome or part thereof, which has been introduced into the genome of a melon plant by transformation, such as Agrobacterium mediated transformation. A plant comprising a transgene stably integrated into its genome is referred to as "transgenic plant". A transgene or transgenic plant may also contain a complete recombinant chromosome or part of a recombinant chromosome, e.g. the part comprising the Wf-allele, introduced into the genome by transformation.

An "isolated nucleic acid sequence" or "isolated DNA" refers to a nucleic acid sequence which is no longer in the natural environment from which it was isolated, e.g. the nucleic acid sequence in a bacterial host cell or in the plant nuclear or plastid genome.

A "host cell" or a "recombinant host cell" or "transformed cell" are terms referring to a new individual cell (or organism) arising as a result of at least one nucleic acid molecule, having been introduced into said cell. The host cell is preferably a plant cell or a bacterial cell. The host cell may contain the nucleic acid as an extra-chromosomally (episomal) replicating molecule, or comprises the nucleic acid integrated in the nuclear or plastid genome of the host cell, or as introduced chromosome, e.g. minichromosome.

"Sequence identity" can be determined by alignment of two peptide or two nucleotide sequences using global or local alignment algorithms. Sequences may then be referred to as "substantially identical" or "essentially similar" when they are optimally aligned by for example the programs GAP or BESTFIT or the Emboss program "Needle" (using default parameters, see below) share at least a certain minimal percentage of sequence identity (as defined further below). These programs use the Needleman and Wunsch global alignment algorithm to align two sequences over their entire length, maximizing the number of matches and minimises the number of gaps. Generally, the default parameters are used, with a gap creation penalty=10 and gap extension penalty=0.5 (both for nucleotide and protein alignments). For nucleotides the default scoring matrix used is DNAFULL and for proteins the default scoring matrix is Blosum62 (Henikoff & Henikoff, 1992, PNAS 89, 10915-10919). Sequence alignments and scores for percentage sequence identity may for example be determined using computer programs, such as EMBOSS as available on the world wide web under ebi.ac.uk/Tools/psa/emboss_needle/). Alternatively sequence similarity or identity may be determined by searching against databases such as FASTA, BLAST, etc., but hits should be retrieved and aligned pairwise to compare sequence identity. Two proteins or two protein domains, or two nucleic acid sequences have "substantial sequence identity" if the percentage sequence identity is at least 85%, 90%, 95%, 98%, 99% or more (e.g. at least 99.1, 99.2 99.3 99.4, 99.5, 99.6, 99.7, 99.8, 99.9 or more (as determined by Emboss "needle" using default parameters, i.e. gap creation penalty=10, gap extension penalty=0.5, using scoring matrix DNAFULL for nucleic acids an Blosum62 for proteins).

DETAILED DESCRIPTION OF THE INVENTION

The present invention relates to a cultivated *Cucumis melo* plant comprising resistance against *Bemisia tabaci* biotype B (referred to herein as Wf resistance). In particular, the resistance is conferred by an introgression fragment on cultivated melon chromosome 11, wherein said introgression fragment is from a wild plant of the species *Cucumis melo* or from a wild relative of melon.

The present inventors crossed two different wild *C. melo* accessions, representative seeds of which were deposited under NCIMB 41965 and NCIMB 41966, to a Wf-susceptible melon breeding line of cantaloupe background and to a Wf-susceptible melon breeding line of canary background, respectively, and carried out QTL-mapping.

Surprisingly, in both mapping populations, a highly significant QTL for Wf-resistance was found on melon chromosome 11, indicating that different wild *Cucumis melo* accessions comprise a Wf-resistance locus on chromosome 11, which was transferred into cultivated *C. melo* and conferred Wf-resistance onto the cultivated melon plant. In the two mapping populations the QTL, which was named Wf_11.1, explained 49.7% and 57.9% of the observed phenotypic variation for Wf resistance and is, therefore, highly significant. Two cultivated melon plants which comprise different size introgressions of the Wf_11.1 QTL in homozygous form (i.e. two recombinants; comprising a recombinant chromosome 11) have been deposited under accession numbers NCIMB 42220 and NCIMB 42221. NCIMB 42220 comprises the Wf_11.1 QTL from NCIMB41966 and NCIMB42221 comprises the Wf_11.1 QTL from wild accession NCIMB41965. Both show high field resistance against *B. tabaci* Biotype B, as seen in the (statistically) significantly reduced average number of $3^{rd}$ instar nymphs and average number of adult whiteflies compared to the average numbers found on the susceptible parents lacking the introgression.

Reference herein to an introgression fragment on chromosome 11 having a QTL or an Wf-resistance conferring locus (or resistance-conferring part thereof) encompasses that the introgression fragment comprises all parts of the resistance-conferring locus needed to confer Wf-resistance. In cases of smaller introgression fragments, the introgression fragment is at least a large enough introgression region so that Wf-resistance is conferred by the introgression fragment when the introgression fragment is in heterozygous or homozygous form in the *C. melo* genome. So, when the introgression fragment is present in, or transferred into, a Wf susceptible melon line or variety, the otherwise susceptible line or variety becomes resistant against Wf as determinable by a Wf-resistance assay. The presence of the introgression fragment in the DNA of the cells, tissues or organs of the melon plant can be confirmed by detecting the presence of the resistant genotype of one or more SNP markers described herein, e.g. in the Wf marker assay. It is noted that the presence of one or more of the molecular markers is a tool to confirm the presence of the introgression fragment on chromosome 11 in phenotypically resistant plants and/or to differentiate the instant plants from other phenotypically resistant plants (which e.g. have Wf resistance on other chromosomes). As different size introgression fragments are encompassed herein not all markers need to be present, and the presence of at least one of the markers is sufficient. The introgression is found in the lower half of the chromosome 11 map, below the ICuGI SNP marker Ps_24-E03, as shown in FIG. 1, especially starting from and/or below marker mME20364.

Thus, in one aspect a cultivated melon plant is provided which comprises Wf-resistance (as determinable in a Wf-resistance assay) and which comprises the resistant genotype of one or more (2, 3, 4, 5, 6, 7, 8, 9, 10, 11, 12, 13, or more) of the markers selected from the group consisting of: mME20364 and/or mME17490 and/or mME15248 and/or mME17306 and/or mME26059 and/or mME38084 and/or mME21974 and/or mME12777 and/or mME15151 and/or mME26139 and/or mME48762 and/or mME25039 and/or mME40109 and/or of any wild melon or wild-relative of melon genome-specific marker in-between SNP markers mME20364 and mME40109, such as in between any two of the aforementioned markers.

As mentioned, different size introgression fragments can equally confer resistance, so that the presence of the resistant genotype of one or more markers of the following groups and sub-groups is encompassed herein [each group and subgroup listed under a) to zzz) represents a different aspect of the invention]:

a) Marker mME20364 and/or marker mME40109 and/or any marker in between mME20364 and mME40109;
b) Marker mME20364 and/or mME25039 and/or any marker in between mME20364 and mME25039;
c) Marker mME20364 and/or mME48762 and/or any marker in between mME20364 and mME48762;
d) Marker mME20364 and/or mME26139 and/or any marker in between mME20364 and mME26139;
e) Marker mME20364 and/or mME15151 and/or any marker in between mME20364 and mME15151;
f) Marker mME20364 and/or mME12777 and/or any marker in between mME20364 and mME12777;
g) Marker mME20364 and/or mME21974 and/or any marker in between mME20364 and mME21974;
h) Marker mME20364 and/or mME38084 and/or any marker in between mME20364 and mME38084;
i) Marker mME20364 and/or mME26059 and/or any marker in between mME20364 and mME26059;
j) Marker mME20364 and/or mME17306 and/or any marker in between mME20364 and mME17306;
k) Marker mME20364 and/or mME15248 and/or any marker in between mME20364 and mME15248;
l) Marker mME20364 and/or mME17490 and/or any marker in between mME20364 and mME17490.
m) Marker mME17490 and/or marker mME40109 and/or any marker in between mME17490 and mME40109;
n) Marker mME17490 and/or mME25039 and/or any marker in between mME17490 and mME25039;
o) Marker mME17490 and/or mME48762 and/or any marker in between mME17490 and mME48762;
p) Marker mME17490 and/or mME26139 and/or any marker in between mME17490 and mME26139;
q) Marker mME17490 and/or mME15151 and/or any marker in between mME17490 and mME15151;
r) Marker mME17490 and/or mME12777 and/or any marker in between mME17490 and mME12777;
s) Marker mME17490 and/or mME21974 and/or any marker in between mME17490 and mME21974;
t) Marker mME17490 and/or mME38084 and/or any marker in between mME17490 and mME38084;
u) Marker mME17490 and/or mME26059 and/or any marker in between mME17490 and mME26059;
v) Marker mME17490 and/or mME17306 and/or any marker in between mME17490 and mME17306;
w) Marker mME17490 and/or mME15248 and/or any marker in between mME17490 and mME15248;
x) Marker mME15248 and/or marker mME40109 and/or any marker in between mME15248 and mME40109;
y) Marker mME15248 and/or mME25039 and/or any marker in between mME15248 and mME25039;
z) Marker mME15248 and/or mME48762 and/or any marker in between mME15248 and mME48762;
aa) Marker mME15248 and/or mME26139 and/or any marker in between mME15248 and mME26139;
bb) Marker mME15248 and/or mME15151 and/or any marker in between mME15248 and mME15151;
cc) Marker mME15248 and/or mME12777 and/or any marker in between mME15248 and mME12777;
dd) Marker mME15248 and/or mME21974 and/or any marker in between mME15248 and mME21974;
ee) Marker mME15248 and/or mME38084 and/or any marker in between mME15248 and mME38084;
ff) Marker mME15248 and/or mME26059 and/or any marker in between mME15248 and mME26059;
gg) Marker mME15248 and/or mME17306 and/or any marker in between mME15248 and mME17306;
hh) Marker mME17306 and/or marker mME40109 and/or any marker in between mME17306 and mME40109;
ii) Marker mME17306 and/or mME25039 and/or any marker in between mME17306 and mME25039;
jj) Marker mME17306 and/or mME48762 and/or any marker in between mME17306 and mME48762;
kk) Marker mME17306 and/or mME26139 and/or any marker in between mME17306 and mME26139;
ll) Marker mME17306 and/or mME15151 and/or any marker in between mME17306 and mME15151;
mm) Marker mME17306 and/or mME12777 and/or any marker in between mME17306 and mME12777;
nn) Marker mME17306 and/or mME21974 and/or any marker in between mME17306 and mME21974;
oo) Marker mME17306 and/or mME38084 and/or any marker in between mME17306 and mME38084;
pp) Marker mME17306 and/or mME26059 and/or any marker in between mME17306 and mME26059;
qq) Marker mME26059 and/or marker mME40109 and/or any marker in between mME26059 and mME40109;
rr) Marker mME26059 and/or mME25039 and/or any marker in between mME26059 and mME25039;
ss) Marker mME26059 and/or mME48762 and/or any marker in between mME26059 and mME48762;
tt) Marker mME26059 and/or mME26139 and/or any marker in between mME26059 and mME26139;
uu) Marker mME26059 and/or mME15151 and/or any marker in between mME26059 and mME15151;
vv) Marker mME26059 and/or mME12777 and/or any marker in between mME26059 and mME12777;
ww) Marker mME26059 and/or mME21974 and/or any marker in between mME26059 and mME21974;
xx) Marker mME26059 and/or mME38084 and/or any marker in between mME26059 and mME38084;
yy) Marker mME38084 and/or marker mME40109 and/or any marker in between mME38084 and mME40109;
zz) Marker mME38084 and/or mME25039 and/or any marker in between mME38084 and mME25039;

aaa) Marker mME38084 and/or mME48762 and/or any marker in between mME38084 and mME48762;
bbb) Marker mME38084 and/or mME26139 and/or any marker in between mME38084 and mME26139;
ccc) Marker mME38084 and/or mME15151 and/or any marker in between mME38084 and mME15151;
ddd) Marker mME38084 and/or mME12777 and/or any marker in between mME38084 and mME12777;
eee) Marker mME38084 and/or mME21974 and/or any marker in between mME38084 and mME21974;
fff) Marker mME21974 and/or marker mME40109 and/or any marker in between mME21974 and mME40109;
ggg) Marker mME21974 and/or mME25039 and/or any marker in between mME21974 and mME25039;
hhh) Marker mME21974 and/or mME48762 and/or any marker in between mME21974 and mME48762;
iii) Marker mME21974 and/or mME26139 and/or any marker in between mME21974 and mME26139;
jjj) Marker mME21974 and/or mME15151 and/or any marker in between mME21974 and mME15151;
kkk) Marker mME21974 and/or mME12777 and/or any marker in between mME21974 and mME12777;
lll) Marker mME12777 and/or marker mME40109 and/or any marker in between mME12777 and mME40109;
mmm) Marker mME12777 and/or mME25039 and/or any marker in between mME12777 and mME25039;
nnn) Marker mME12777 and/or mME48762 and/or any marker in between mME12777 and mME48762;
ooo) Marker mME12777 and/or mME26139 and/or any marker in between mME12777 and mME26139;
ppp) Marker mME12777 and/or mME15151 and/or any marker in between mME12777 and mME15151;
qqq) Marker mME15151 and/or marker mME40109 and/or any marker in between mME15151 and mME40109;
rrr) Marker mME15151 and/or mME25039 and/or any marker in between mME15151 and mME25039;
sss) Marker mME15151 and/or mME48762 and/or any marker in between mME15151 and mME48762;
ttt) Marker mME15151 and/or mME26139 and/or any marker in between mME15151 and mME26139;
uuu) Marker mME26139 and/or marker mME40109 and/or any marker in between mME26139 and mME40109;
vvv) Marker mME26139 and/or mME25039 and/or any marker in between mME26139 and mME25039;
www) Marker mME26139 and/or mME48762 and/or any marker in between mME26139 and mME48762;
xxx) Marker mME48762 and/or marker mME40109 and/or any marker in between mME48762 and mME40109;
yyy) Marker mME48762 and/or mME25039 and/or any marker in between mME48762 and mME25039;
zzz) Marker mME25039 and/or marker mME40109 and/or any marker in between mME25039 and mME40109;

Markers "in between" the above mentioned markers are for example those which are positioned in between those markers as seen in FIG. 1, or other markers that are not explicitly shown in FIG. 1, but which are also flanked by the marker pairs mentioned. The skilled person can easily identify new markers in the genomic region or subgenomic region being flanked by any of the marker pairs listed above. Such markers need not to be SNP markers, but can be any type of genotypic or phenotypic marker mapped to that genomic or subgenomic region. Preferably such markers are genetically and physically linked to the Wf_11.1 QTL as present in (and as derivable from) at least wild accessions NCIMB 41965 and NCIMB41966, but preferably also as present in other wild melons or wild relatives of melon which comprise Wf resistance. In other words, the markers are preferably indicative of the presence of the QTL on chromosome 11 in a non-source specific manner.

As can be seen in FIG. 1, three markers are population (source) specific, i.e. found only in one of the resistance sources. These are markers mME17011, which is linked to QTL Wf_11.1 originating from resistance source NCIMB41965 and markers mME22724 and mME21134, which are linked to QTL Wf_11.1 originating from resistance source NCIMB 41966. Such source specific markers can of course also be used to identify and/or transfer the Wf_11.1 QTL derived from that source. Other source specific markers can be developed by the skilled person.

Thus, in one aspect a cultivated melon plant is provided which comprises Wf resistance (as determinable in a Wf-resistance assay) and which comprises the resistant genotype of one or more (2, 3, 4, 5, 6, 7, 8, 9, 10, 11, 12, 13, or more) of the markers selected from the groups consisting of: mME20364 and/or mME17490 and/or mME15248 and/or mME17306 and/or mME26059 and/or mME38084 and/or mME21974 and/or mME12777 and/or mME15151 and/or mME26139 and/or mME48762 and/or mME25039 and/or mME40109 and/or any wild melon or wild-relative of melon genome-specific marker in between SNP markers mME20364 and mME40109.

In another aspect a cultivated melon plant is provided which comprises Wf resistance (as determinable in a Wf-resistance assay) and which comprises the resistant genotype of one or more (2, 3, 4, 5, 6, 7, 8, 9, 10, 11, 12, 13, or more) of the markers selected from the groups consisting of those groups listed in a) to zzz) above.

The resistance genotype of each of the markers refers to the genotype present in the plant comprising the Wf_11.1 QTL in homozygous or heterozygous form. The resistance genotype of the markers is shown herein below:

| Marker name | SNP (Single Nucleotide Poly-morphism) | Resistance genotype (NCIMB41966) | Resistance genotype (NCIMB41965) | Resistance genotype when introgression comprising Wf_11.1 is in heterozygous form |
|---|---|---|---|---|
| Population non-specific (common) markers | | | | |
| mME20364 | [C/T] | C:C | C:C | C:T |
| mME17490 | [A/G] | A:A | A:A | A:G |
| mME15248 | [C/T] | C:C | C:C | C:T |
| mME17306 | [C/T] | C:C | C:C | C:T |
| mME26059 | [A/T] | A:A | A:A | A:T |
| mME38084 | [A/G] | G:G | G:G | G:A |
| mME21974 | [A/C] | C:C | A:C | A:C |
| mME12777 | [C/T] | C:C | C:C | C:T |
| mME15151 | [A/G] | G:G | G:G | G:A |
| mME26139 | [A/C] | C:C | C:C | C:A |
| mME48762 | [A/C] | C:C | C:C | C:A |
| mME25039 | [T/C] | C:C | C:C | C:T |
| mME40109 | [C/T] | T:T | T:T | T:C |
| Population specific markers | | | | |
| mME17011 | [C/T] | — | T:T | T:C |
| mME22724 | [A/G] | A:A | — | A:G |
| mME21134 | [C/T] | T:T | — | T:C |

As the resistance is dominant, also the heterozygous introgression confers resistance. Thus, the presence of the introgression fragment is determinable by the presence of the resistance genotype of one or more markers, whereby the resistance genotype may be the single nucleotide in homozygous form (e.g. CC for mME20364) or in heterozygous form (e.g. CT for mME20364). The susceptible genotype is homozygous for the other nucleotide (for mME20364 this is TT).

In one aspect a cultivated melon plant is provided herein, which is resistant against whitefly due to the presence of a recombinant chromosome 11. The recombinant chromosome 11 comprises an introgression fragment which comprises a Wf resistance conferring QTL, as determinable by the presence of a resistance genotype of one or more of the markers listed herein above. Thus, plants with varying sizes of resistance conferring introgressions are encompassed herein.

Exemplary are cultivated melon plants comprising a recombinant chromosome 11 and/or an introgression fragment on chromosome 11 as present in seeds deposited under accession number NCIMB 42221 or NCIMB 42220, or progeny (descendants) thereof which retain the Wf resistance QTL. However, the skilled person can easily make other cultivated melon plants comprising the Wf resistance QTL of the invention.

Plants deposited under accession number NCIMB 42221 (comprising an introgression fragment on chromosome 11 derivable from NCIMB 41965) comprise an introgression fragment of about 33 cM. The introgression fragment is in homozygous form and is detectable by (the resistance genotype of) one or more markers selected from the group: mME17490 and/or mME15248 and/or mME17306 and/or mME26059 and/or mME38084 and/or mME21974 and/or mME12777 and/or mME17011 and/or mME15151 and/or mME26139 and/or mME48762 and/or mME25039 and/or mME40109 and/or of any wild melon or wild-relative of melon genome-specific marker in-between SNP markers mME 17490 and mME40109, such as in between any two of the aforementioned markers (see also FIG. 1). This plant comprises field resistance against *B. tabaci*, as shown in the Examples.

Plants deposited under accession number NCIMB 42220 (comprising an introgression fragment on chromosome 11 derivable from NCIMB 41966) comprise an introgression fragment of about 34 cM. The introgression fragment is in homozygous form and is detectable by (the resistance genotype of) one or more markers selected from the group: mME22724 and/or mME15248 and/or mME17306 and/or mME26059 and/or mME38084 and/or mME21974 and/or of any wild melon or wild-relative of melon genome-specific marker in-between SNP markers mME22724 and mME21974, such as in between any two of the aforementioned markers (see also FIG. 1). This plant comprises field resistance against *B. tabaci*, as shown in the Examples.

Therefore, in one aspect a cultivated melon plant is provided comprising whitefly resistance due to a recombinant chromosome 11, said recombinant chromosome 11 comprises a resistance genotype of one or more markers selected from a) to zzz) above.

In one aspect the plant comprises a resistance genotype of one or more markers selected from m) to zzz) above (as exemplified by deposit NCIMB 42221 or progeny thereof which retain the introgression fragment or resistance conferring part thereof).

In another aspect the plant comprises a resistance genotype of one or more markers selected from s), t), u), v), w), dd), ee), ff), gg), nn), oo), pp), ww), xx) or eee) above (as exemplified by deposit NCIMB 42220 or progeny thereof which retain the introgression fragment or resistance conferring part thereof).

Progeny (descendants obtained by selfing and/or crossing) of a plant comprising a recombinant chromosome 11 as described herein may either retain the same size introgression fragment as in the parent plant or may comprise smaller size introgression fragments, which however still confer the *B. tabaci* resistance phenotype. The smaller introgression fragment, therefore, retains the resistance conferring part of the introgression fragment and the markers on that fragment, e.g. any one or more markers (group of markers) listed in a) to zzz) or, in case of descendants of NCIMB 42220 or NCIMB 42221 any one or more markers (group of markers) listed in s), t), u), v), w), dd), ee), ff), gg), nn), oo), pp), ww), xx) or eee) for descendants of NCIMB 42220 or listed in m) to zzz) for descendants of NCIMB 42221.

Thus, in one aspect, it was found that a Quantitative Trait Loci (QTL Wf_11.1) which confers *B. tabaci*-resistance is present on chromosome 11 of wild melons and that this QTL, when transferred (introgressed) into a cultivated, *B. tabaci*-susceptible melon variety or breeding line, and when present in heterozygous or homozygous form, confers *B. tabaci*-resistance onto the cultivated melon plant. The QTL, or the introgression fragment comprising the QTL (comprising the Wf-resistance allele), is thus dominant, i.e. it is sufficient to have the introgression fragment on one of the chromosomes 11 (one recombinant chromosome 11), while the homologous chromosome 11 of the pair may be a (non-recombinant) chromosome 11 of cultivated *C. melo* lacking the introgression fragment.

Although the present sources of Wf-resistance allele introgressions are two wild sources (NCIMB 41965 and NCIMB 41966, from unknown origin and from India), there are likely other wild *Cucumis* accessions which comprise Wf-resistance alleles or Wf orthologous alleles at the same locus on chromosome 11. Such Wf-resistance alleles or Wf-resistance orthologous alleles can also be identified and introgressed into cultivated *C. melo* as described herein, to generate a cultivated *C. melo* plant comprising a genome of *C. melo* and a recombinant chromosome 11, whereby the recombinant chromosome 11 comprises a wild *Cucumis* species introgression fragment, which confers an Wf-resistance phenotype onto the cultivated *C. melo* plant when present in homozygous or heterozygous form.

Accessions of wild melons and wild relatives of melon, such as accessions obtainable from the USDA National Plant Germplasm System collection or other germplasm collections, can be screened for *B. tabaci* biotype B resistance using phenotypic and/or Wf-marker assays, and resistant accessions can be crossed with a *Cucumis melo* plant lacking *B. tabaci* resistance. The F2 generation (or further generation, such as the F3, F4, etc. and/or a backcross generations) can then be screened for recombinant plants having the Wf-resistance phenotype and/or the introgression fragment or a resistance conferring part thereof, using the molecular marker assays (Wf marker assay) described herein.

Plants, Seeds and Plant Parts According to the Invention

Thus, in an embodiment a cultivated *Cucumis melo* plant comprising resistance against *Bemisia tabaci* biotype B (W) is provided.

The presence of a Wf-resistance phenotype can be determined using the Wf resistance assay (e.g. vide infra), whereby plants are screened for resistance in the field or controlled environment using known methods. Importantly, sufficient plants (e.g. at least 10, 15, 20 or more) of a line or variety are included in sufficient replicates (e.g. at least 2, 3, 4 or more). Also suitable controls should be included, such as susceptible varieties or susceptible lines. Examples of *B. tabaci* susceptible controls are the Piel de Sapo variety Medellin F1 (Nunhems) and the Western Shipper variety Caribbean Gold F1 (Rijk Zwaan).

In the Wf-resistance assay plants are grown under the same environmental conditions, exposed to *B. tabaci* (e.g. natural field infestation), either the average number of nymphs (3$^{rd}$ instar) and/or the average number of adult whiteflies for each line or variety are determined at one or more time-points. Average disease scores can then be calculated for a line or variety. When the average number of nymphs and/or adult whiteflies is (statistically) significantly lower on the line or variety comprising the recombinant chromosome 11 compared to the susceptible control(s), such as the variety Medellin F1, that line or variety comprises a Wf-resistance phenotype of the invention. In one aspect, the average number of 3$^{rd}$ instar nymphs and/or of adult whiteflies is 60% or less than that of the susceptible control, preferably, it is 50% or less, 40% or less, 35% or less, 30% or less, 20% or less, or 10% or less of the average number found on the susceptible control variety when grown under the same conditions.

The resistance against Wf is conferred by an introgression fragment on chromosome 11, wherein the introgression fragment is derived from a wild melon genome or from a wild relative of melon. The introgression fragment comprises the Quantitative Trait Locus (QTL) referred herein to as Wf_11.1, which locus in turn comprises a Wf-resistance allele, or a Wf-orthologous resistance allele, of the Wf-resistance gene.

The cultivated melon plants according to the invention, thus, have a recombinant chromosome 11, which comprises an introgression fragment of a wild melon chromosome 11 or of an orthologous chromosome 11 of a wild relative of melon.

As the resistance is dominant, the resistance phenotype is seen when the resistance allele is in heterozygous or homozygous form, the cultivated melon plants according to the invention have the introgression fragment, or the resistance-conferring part thereof, on chromosome 11 in heterozygous or homozygous form.

The introgression fragment is derivable from (or derived from) or obtainable from (or obtained from) a wild plant of the species *Cucumis melo*, which comprises the Wf QTL (Wf_11.1) on chromosome 11. Alternatively, the introgression fragment is derivable from (or derived from) or obtainable from (obtained from) a wild relative of *Cucumis melo*, which can be crossed with *Cucumis melo* (optionally using embryo rescue or other techniques to aid production of viable offspring), so that the fragment of the orthologous chromosome 11 can be introgressed into the chromosome 11 of *C. melo*, especially cultivated *C. melo*.

In a specific embodiment, the introgression fragment comprising the *B. tabaci* resistance locus is derivable from (or derived from) or obtainable from (or obtained from) wild *C. melo* plants, a representative sample of seeds of which has been deposited under accession number NCIMB 41965 or NCIMB41966. In one aspect the invention provides a cultivated *C. melo* plant which comprises resistance against *B. tabaci* biotype B, wherein the resistance is conferred by an introgression fragment on melon chromosome 11, wherein said introgression fragment (conferring said Wf resistance) is obtained by (or obtainable by) crossing a plant of which seeds were deposited under Accession number NCIMB 41965 or NCIMB41966 with a cultivated melon plant. Both these wild *C. melo* accessions have a Wf-resistance phenotype as shown in the Examples.

The introgression fragment may also be derived from (or obtained from) other wild *C. melo* plants or other wild relatives of melon, which have a Wf-resistance phenotype and which comprise one or more of the markers described in Table 1 and listed in a) to zzz) further above.

The skilled person is capable of identifying and introgressing the Wf_11.1 QTL-comprising region found in other wild melon accessions or in other wild relatives of melon into cultivated *C. melo*, as will be explained further below. The skilled person is also able to identify other molecular markers linked to (associated with) the QTL, which can be used to identify the presence of an introgression fragment from such other wild melons or wild relatives of melon on chromosome 11 of *C. melo*. The molecular markers provided herein were found to be associated with the Wf-resistance QTL, where the introgression fragment was obtained from two different wild sources. These markers may also be linked to (associated with) Wf-resistance on chromosome 11, or on orthologous chromosomes 11, and may thus be useful to derive the QTL from different sources. Alternatively, the skilled person can identify other molecular markers using known methods.

In one embodiment the presence of the introgression fragment, or the chromosome 11 region (or orthologous chromosome 11 region), comprising the Wf-resistance locus, is detectable by a molecular marker assay which detects at least one, or at least 2, 3, 4, 5, 6, 7, 8, 9, 10, 11, 12, 13, 14 or more of the following Single Nucleotide Polymorphism (SNP) markers:

a) the CC genotype or CT genotype for the SNP marker mME20364 in SEQ ID NO: 1;
b) the AA genotype or AG genotype for the SNP marker mME17490 in SEQ ID NO: 2;
c) the CC genotype or CT genotype for the SNP marker mME15248 in SEQ ID NO: 3;
d) the CC genotype or CT genotype for SNP marker mME17306 in SEQ ID NO: 4;
e) the AA genotype or AT genotype for SNP marker mME26059 in SEQ ID NO: 5;
f) the GG genotype or GA genotype for SNP marker mME38084 in SEQ ID NO: 6;
g) the CC genotype or AC genotype for SNP marker mME21974 in SEQ ID NO: 7;
h) the CC genotype or CT genotype for SNP marker mME12777 in SEQ ID NO: 8;
i) the GG genotype or GA genotype for SNP marker mME15151 in SEQ ID NO: 9;
j) the CC genotype or CA genotype for SNP marker mME26139 in SEQ ID NO: 10;
k) the CC genotype or CA genotype for SNP marker mME48762 in SEQ ID NO: 11;
l) the CC genotype or CT genotype for SNP marker mME25039 in SEQ ID NO: 12;
m) the TT genotype or TC genotype for SNP marker mME40109 in SEQ ID NO: 13;
n) any wild melon or wild-relative of melon genome-specific marker as listed in a) to zzz) above.

As mentioned, these SNP markers were found to be genetically linked to (or associated with) the introgression fragment on chromosome 11 comprising the QTL Wf 11.1 in both mapping populations, i.e. in plants comprising the resistance QTL from two different wild melon accessions.

When reference herein is made to a certain SNP genotype in a specific genomic sequence (selected e.g. from SEQ ID NO: 1 to SEQ ID NO: 13), this encompasses also the SNP genotype in variants of the genomic sequence, i.e. the SNP genotype in a genomic sequence comprising at least 90%, 95%, 98%, 99% (substantial) sequence identity or more to the sequence referred to (selected e.g. from SEQ ID NO: 1 to SEQ ID NO: 13). Thus any reference herein to any one of SEQ ID NO: 1 to 13 in one aspect also encompasses a variant of any one of SEQ ID NO: 1 to 13, said variant comprising at least 85%, 90%, 95%, 98%, 99% sequence identity or more to said sequence (using e.g. the program 'Needle').

Thus, in one embodiment the Wf-resistant cultivated melon plants according to the invention comprise at least one Cytosine (CC or CT genotype) instead of two Thymines (TT genotype) at nucleotide 51 of SEQ ID NO: 1 (referred to as SNP marker mME20364); and/or they comprise at least one Adenine (AA or AG genotype) instead of two Guanines (GG genotypes) at nucleotide 35 of SEQ ID NO: 2 (referred to as SNP marker mME17490); and/or they comprise at least one Cytosines (CC or CT genotype) instead of two Thymines (TT genotype) at nucleotide 34 of SEQ ID NO: 3 (referred to as SNP marker mME15248); and/or they comprise at least one Cytosine (CC or CT genotype) instead of two Thymines (TT genotype) at nucleotide 51 of SEQ ID NO: 4 (referred to as SNP marker mME17306); and/or they comprise at least one Adenine (AA or AT genotype) instead of two Thymines at nucleotide 51 of SEQ ID NO:5 (referred to as SNP marker mME26059); and/or they comprise at least one Guanine (GG or GA genotype) instead of two Adenines (AA genotype) at nucleotide 33 of SEQ ID NO: 6 (referred to as SNP marker mME38084); and/or they comprise at least one Cytosine (e.g. CC or CA genotype) instead of two Adenines (AA genotype) at nucleotide 51 of SEQ ID NO: 7 (referred to as SNP marker mME21974); and/or they comprise at least one Cytosine (CC or CT genotype) instead of two Thymines (TT genotype) at nucleotide 51 of SEQ ID NO: 8 (refereed herein to as SNP marker mME12777); and/or they comprise at least one Guanine (GG or GA genotypes) instead of two Adenines (AA genotype) at nucleotide 51 of SEQ ID NO: 9 (referred to as SNP marker mME15151); and/or they comprise at least one Cytosine (CC or CA genotypes) instead of two Adenines (AA genotype) at nucleotide 51 of SEQ ID NO: 10 (referred to as SNP marker mME26139); and/or they comprise at least one Cytosines (CC or CA genotype) instead of two Adenines (AA genotype) at nucleotide 51 of SEQ ID NO: 11 (referred to as SNP marker mME48762); and/or they comprise at least one Cytosines (CC or CT genotype) instead of two Thymines (TT genotype) at nucleotide 51 of SEQ ID NO: 12 (referred to as SNP marker mME25039); and/or they comprise at least one Thymine (TT or TC genotype) instead of two Cytosines (CC genotype) at nucleotide 51 of SEQ ID NO: 13 (referred to as SNP marker mME40109), or any wild melon or wild-relative of melon genome-specific marker as listed in groups a) to zzz) above.

The SNP genotype refers to two nucleotides, and genomic sequences comprising one of these two nucleotides, one on each chromosome 11 of the chromosome pair. So a plant having a CC genotype for mME20364 has an identical nucleotide (C) on both chromosomes at nucleotide 51 of SEQ ID NO:1, while a plant having an AC genotype for mME21974 has one chromosome with an A at nucleotide 51 of SEQ ID NO: 7 and one chromosome with a C at nucleotide 51 of SEQ ID NO: 7.

The skilled person can easily identify any wild melon or wild-relative of melon genome-specific marker as listed in a) to zzz) above. This can for example be done by sequencing genomic regions in-between any of the markers mentioned herein or by mapping new markers to a region in between any of the marker regions or sub-regions listed in groups a) to zzz). Preferably, but not necessarily, such markers are common markers, i.e. they are present on chromosome 11 of more than one QTL Wf_11.1 resistance source, e.g. they are present in at least two or more Wf resistance sources, such as in NCIMB 41965 and/NCIMB 41966 and/or any other wild melon or wild relative of melon which has Wf resistance due to a QTL on chromosome 11.

Three markers were found in only one of the two populations, namely markers mME17011, mME22724 and mME21134 (see FIG. 1). These markers are, therefore, not 'common' markers, but population specific markers. Obviously, such non-common markers can equally be used in identifying and/or selecting plants comprising an introgression fragment on chromosome 11 having QTL Wf_11.1 and/or transferring an introgression fragment comprising QTL Wf_11.1 from one melon plant into the genome of another melon plant (e.g. into a whitefly susceptible cultivated melon plant). Also, such herein 'non-common' markers may very well be/become common markers if they are also found in other Wf resistant plants comprising the Wf_11.1 QTL.

Marker mME17011 was found only in the population derived from NCIMB 41965, such as cultivated melon representative seeds of which were deposited under accession number NCIMB 42221. The marker is located in between makers mME12777 and mME15151 and falls therefore into the groups a)-e), m)-q), x)-bb), hh)-ll), qq)-uu), yy)-ccc), fff)-jjj) and lll)-ppp), as described above. The resistance genotype of mME17011 can be detected by at least one Thymine (TT or TC genotype) instead of two Cytosines (CC genotype) at nucleotide 51 of SEQ ID NO: 66.

Markers mME22724 and mME21134 were only found in the population derived from NCIMB 41966, such as cultivated melon representative seeds of which were deposited under accession number NCIMB 42220. The marker mME22724 is located in between makers mME1749 and mME15248 and falls therefore into the groups a)-k) and m)-w). The marker mME21134 is located in between makers mME12777 and mME15151 and falls therefore into the groups a)-e), m)-q), x)-bb), hh)-ll), qq)-uu), yy)-ccc), fff)-jjj) and lll)-ppp), as described above. The resistance genotype can be detected by at least one Adenine (AA or AG genotype) instead of two Guanines (GG genotype) at nucleotide 44 of SEQ ID NO: 67 (for marker mME22724) or by at least one Thymine (TT or TC genotype) instead of two Cytosines (CC genotype) at nucleotide 51 of SEQ ID NO: 68.

Thus in one embodiment the presence of the introgression fragment, or the chromosome 11 region (or orthologous chromosome 11 region), comprising the Wf-resistance locus, is detectable by a molecular marker assay which detects at least one, or at least 2, 3, 4, 5, 6, 7, 8, 9, 10, 11, 12, 13, 14, or more of the following Single Nucleotide Polymorphism (SNP) markers:

a) the CC genotype or CT genotype for the SNP marker mME20364 in SEQ ID NO: 1;
b) the AA genotype or AG genotype for the SNP marker mME17490 in SEQ ID NO: 2;
c) the CC genotype or CT genotype for the SNP marker mME15248 in SEQ ID NO: 3;
d) the CC genotype or CT genotype for SNP marker mME17306 in SEQ ID NO: 4;
e) the AA genotype or AT genotype for SNP marker mME26059 in SEQ ID NO: 5;
f) the GG genotype or GA genotype for SNP marker mME38084 in SEQ ID NO: 6;
g) the CC or AC genotype for SNP marker mME21974 in SEQ ID NO: 7;
h) the CC genotype or CT genotype for SNP marker mME12777 in SEQ ID NO: 8;

i) the GG genotype or GA genotype for SNP marker mME15151 in SEQ ID NO: 9;
j) the CC genotype or CA genotype for SNP marker mME26139 in SEQ ID NO: 10;
k) the CC genotype or CA genotype for SNP marker mME48762 in SEQ ID NO: 11;
l) the CC genotype or CT genotype for SNP marker mME25039 in SEQ ID NO: 12;
m) the TT genotype or TC genotype for SNP marker mME40109 in SEQ ID NO: 13;
n) any wild melon or wild-relative of melon genome-specific marker as listed in a) to zzz) above, wherein the wild melon or wild relative of melon genome-specific marker is selected from the group comprising the TT or TC genotype for SNP marker mME17011 at nucleotide 51 of SEQ ID NO: 66; the AA or AG genotype for SNP marker mME22724 at nucleotide 44 in SEQ ID NO: 67; and the TT or TC genotype for SNP marker mME21134 at nucleotide 51 in SEQ ID NO: 68.

Wf-resistant cultivated melon plants comprising at least one marker, preferably at least 2, 3, 4, 5, 6, 7, 8, 9, 10, 11, 12, 13, 14, 15, 16, or more markers, selected from the markers mentioned in any group and sub-groups disclosed herein are encompassed herein.

In a further embodiment the Wf-resistant cultivated melon plants according to the invention comprise at least one Cytosine (CC or CT genotype) instead of two Thymines (TT genotype) at nucleotide 51 of SEQ ID NO: 1 (referred to as SNP marker mME20364); and/or they comprise at least one Adenine (AA or AG genotype) instead of two Guanines (GG genotypes) at nucleotide 35 of SEQ ID NO: 2 (referred to as SNP marker mME17490); and/or they comprise at least one Cytosines (CC or CT genotype) instead of two Thymines (TT genotype) at nucleotide 34 of SEQ ID NO: 3 (referred to as SNP marker mME15248); and/or they comprise at least one Cytosine (CC or CT genotype) instead of two Thymines (TT genotype) at nucleotide 51 of SEQ ID NO: 4 (referred to as SNP marker mME17306); and/or they comprise at least one Adenine (AA or AT genotype) instead of two Thymines at nucleotide 51 of SEQ ID NO:5 (referred to as SNP marker mME26059); and/or they comprise at least one Guanine (GG or GA genotype) instead of two Adenines (AA genotype) at nucleotide 33 of SEQ ID NO: 6 (referred to as SNP marker mME38084); and/or they comprise at least one Cytosine (e.g. CC or CA genotype) instead of two Adenines (AA genotype) at nucleotide 51 of SEQ ID NO: 7 (referred to as SNP marker mME21974); and/or they comprise at least one Cytosine (CC or CT genotype) instead of two Thymines (TT genotype) at nucleotide 51 of SEQ ID NO: 8 (refereed herein to as SNP marker mME12777); and/or they comprise at least one Guanine (GG or GA genotypes) instead of two Adenines (AA genotype) at nucleotide 51 of SEQ ID NO: 9 (referred to as SNP marker mME15151); and/or they comprise at least one Cytosine (CC or CA genotypes) instead of two Adenines (AA genotype) at nucleotide 51 of SEQ ID NO: 10 (referred to as SNP marker mME26139); and/or they comprise at least one Cytosines (CC or CA genotype) instead of two Adenines (AA genotype) at nucleotide 51 of SEQ ID NO: 11 (referred to as SNP marker mME48762); and/or they comprise at least one Cytosines (CC or CT genotype) instead of two Thymines (TT genotype) at nucleotide 51 of SEQ ID NO: 12 (referred to as SNP marker mME25039); and/or they comprise at least one Thymine (TT or TC genotype) instead of two Cytosines (CC genotype) at nucleotide 51 of SEQ ID NO: 13 (referred to as SNP marker mME40109), and/or comprise any wild melon or wild-relative of melon genome-specific marker as listed in groups a) to zzz). In one aspect the wild melon or wild relative of melon genome-specific marker is selected from the group comprising the TT or TC genotype for SNP marker mME17011 at nucleotide 51 of SEQ ID NO: 66; the AA or AG genotype for SNP marker mME22724 at nucleotide 44 in SEQ ID NO: 67; and the TT or TC genotype for SNP marker mME21134 at nucleotide 51 in SEQ ID NO: 68.

In one aspect, the introgression fragment, or the chromosome 11 region (or orthologous chromosome 11 region) comprising the Wf-resistance locus, which is detectable by the above markers is from a wild plant of the species *Cucumis melo*, and in one aspect it is from a plant of which a representative sample of seeds has been deposited under accession number NCIMB 41965 and NCIMB 41966, thus the QTL, and the chromosome 11 region comprising the QTL, is in one aspect the QTL as found in NCIMB 41965 or in NCIMB 41966. In one aspect the introgression fragment, or the recombinant chromosome 11, is obtained from crossing a plant grown from seeds deposited under accession number NCIMB 41965 or NCIMB 41966 with another melon plant, especially a cultivated melon plant of the species *C. melo*. The cultivated melon plant is for example a plant which is susceptible against whitefly. The cultivated melon may be any line, variety or cultivar, such as cantaloupe, Canary, Western Shipper, Eastern Shipper, Charentais, Galia, Honey Dew, Piel de Sapo or other.

Thus, in one aspect the Wf-resistant melon plant according to the invention comprises an introgression fragment on chromosome 11, which is obtainable from seeds of which a representative sample has been deposited under NCIMB 41965 or NCIMB 41966 and wherein the introgression fragment comprises, or is detectable by, at least 1, 2, 3, 4, 5, 6, 7, 8, 9, 10, 11, 12, 13, or more SNP markers selected from the group consisting of
a) the CC genotype or CT genotype for the SNP marker mME20364 in SEQ ID NO: 1;
b) the AA genotype or AG genotype for the SNP marker mME17490 in SEQ ID NO: 2;
c) the CC genotype or CT genotype for the SNP marker mME15248 in SEQ ID NO: 3;
d) the CC genotype or CT genotype for SNP marker mME17306 in SEQ ID NO: 4;
e) the AA genotype or AT genotype for SNP marker mME26059 in SEQ ID NO: 5;
f) the GG genotype or GA genotype for SNP marker mME38084 in SEQ ID NO: 6;
g) the CC or AC genotype for SNP marker mME21974 in SEQ ID NO: 7;
h) the CC genotype or CT genotype for SNP marker mME12777 in SEQ ID NO: 8;
i) the GG genotype or GA genotype for SNP marker mME15151 in SEQ ID NO: 9;
j) the CC genotype or CA genotype for SNP marker mME26139 in SEQ ID NO: 10;
k) the CC genotype or CA genotype for SNP marker mME48762 in SEQ ID NO: 11;
l) the CC genotype or CT genotype for SNP marker mME25039 in SEQ ID NO: 12;
m) the TT genotype or TC genotype for SNP marker mME40109 in SEQ ID NO: 13;
n) any wild melon or wild-relative of melon genome-specific marker as listed in a) to zzz) above.

To obtain the introgression fragment from the deposited seeds, a plant is grown from the seed and the plant is crossed with a susceptible *C. melo* plant to obtain F1 seeds. The F1 hybrid seed and plants grown therefrom, contain one chromosome 11 from the susceptible parent (without QTL Wf_11.1) and one chromosome 11 from the wild Wf-resistant parent. To generate recombination events between these two homologous chromosomes 11, meiosis needs to take place and plants comprising the recombinant chromosomes 11 need to be identified. For example, the F1 can be selfed to produce F2 plants, and/or resistant F2 plants or F3 plants, etc., can be backcrossed to the susceptible parent. Plants which are resistant to whitefly can be screened for, and selected for, the presence of one or more of the above SNP markers in order to identify plants comprising a recombinant chromosome 11, comprising a Wf-resistance conferring introgression fragment from the deposited seeds.

Similarly, cultivated melon plants comprising resistance against whitefly, whereby the resistance is conferred by an introgression fragment on chromosome 11, can be generated and/or identified using different methods. For example, to obtain a cultivated melon plant comprising a Wf-resistance conferring introgression fragment from a wild melon or wild relative of melon, first a wild melon or wild relative of melon is identified which has an whitefly resistance phenotype and/or which comprises one or more of the SNP markers associated with Wf-resistance disclosed herein, e.g. any one, or more, or all of the markers above. The identified plant is crossed with a susceptible C. melo plant to obtain F1 seeds. The F1 hybrid seed and plants grown therefrom, contain one chromosome 11 from the susceptible parent (without QTL Wf_11.1) and one chromosome 11 from the wild Wf-resistant parent. To generate recombination events between these two homologous chromosomes 11, meiosis needs to take place and plants comprising the recombinant chromosomes 11 need to be identified. For example, the F1 can be selfed to produce F2 plants, and/or resistant F2 plants or F3 plants, etc., can be backcrossed to the susceptible parent. Plants which are resistant to whitefly can be screened for, and/or selected for, the presence of one or more of the above SNP markers and/or screened for, and/or selected for, the presence of the Wf-resistance phenotype, in order to identify plants comprising a recombinant chromosome 11, comprising a whitefly resistance conferring introgression fragment from the wild melon or wild relative of melon. Alternatively or in addition, QTL mapping can be carried out in order to identify further molecular markers linked to the QTL Wf_11.1 and/or to generate cultivated C. melo plants comprising an introgression fragment on chromosome 11 which confers whitefly-resistance.

In one embodiment the presence of the introgression fragment, or the chromosome 11 region (or orthologous chromosome 11 region), comprising the whitefly resistance locus, is detectable by a molecular marker assay which detects at least one (or 2, 3, 4, 5, 6, 7, 8, 9, 10, 11, 12, 13, or more) of the following markers:
a) the CC genotype or CT genotype for the SNP marker mME20364 in SEQ ID NO: 1;
b) the AA genotype or AG genotype for the SNP marker mME17490 in SEQ ID NO: 2;
c) the CC genotype or CT genotype for the SNP marker mME15248 in SEQ ID NO: 3;
d) the CC genotype or CT genotype for SNP marker mME17306 in SEQ ID NO: 4;
e) the AA genotype or AT genotype for SNP marker mME26059 in SEQ ID NO: 5;
f) the GG genotype or GA genotype for SNP marker mME38084 in SEQ ID NO: 6;
g) the CC or AC genotype for SNP marker mME21974 in SEQ ID NO: 7;
h) the CC genotype or CT genotype for SNP marker mME12777 in SEQ ID NO: 8;
i) the GG genotype or GA genotype for SNP marker mME15151 in SEQ ID NO: 9;
j) the CC genotype or CA genotype for SNP marker mME26139 in SEQ ID NO: 10;
k) the CC genotype or CA genotype for SNP marker mME48762 in SEQ ID NO: 11;
l) the CC genotype or CT genotype for SNP marker mME25039 in SEQ ID NO: 12;
m) the TT genotype or TC genotype for SNP marker mME40109 in SEQ ID NO: 13;
n) any wild melon or wild-relative of melon genome-specific marker as listed in the groups and/or subgroups of a) to zzz) above;
o) any wild melon or wild relative of melon genome specific marker in-between the marker of a) and the marker of m).

In one aspect, at least one, two, at least three, at least four or more markers are detected from the markers of a) to n) above. In a specific embodiment at least one, two or three markers are detected selected from the group consisting of c) (mME15248), d) (mME17306), e) (mME26059), or any wild melon or wild-relative of melon genome specific marker in between marker b) (mME17490) and h) (mME12777)), e.g. c) and d); c) and e); c) and a marker between b) and h); d) and e); d) and a marker between b) and h); or e) and a marker between b) and h).

Any wild melon or wild-relative of melon genome-specific marker in-between two markers (or flanked by two markers, which can be referred to as flanking markers) refers to (the resistance genotype of) any molecular marker which maps genetically to the chromosome 11 region in-between the markers (see FIG. 1) and/or which lies physically in-between the markers, and which is indicative of the wild melon chromosome 11 region or of the wild-relative of melon chromosome 11 region. This means that the marker is polymorphic between the cultivated melon genome and the wild melon or wild-relative of melon genome. In one aspect, the marker is a Single Nucleotide Polymorphism, but other molecular markers such as RFLP, AFLP, RAPD, DNA sequencing, etc. may equally be used.

As two specific recombinants have been found which comprise two different introgression fragments conferring good resistance against whitefly, as shown in FIG. 1, the presence of at least 1, 2, 3, 4, 5, 6 or more of the markers present in both recombinants is a specific embodiment herein. Thus (the resistance genotype of) any marker in-between marker mME17490 and mME12777 are preferably present and indicative of the QTL Wf_11.1. Examples of such markers are marker mME15248, mME17306, mME26059, mME38048, mME21974 and/or mME12777, and/or others in between the two flanking markers mME17490 and mME12777. Thus, in one aspects at least 1, 2, 3, 4, 5 or 6 markers are present selected from the group consisting of marker mME15248, mME17306, mME26059, mME38048, mME21974 and/or mME12777. In another aspects at least 1, 2, 3, 4, 5, 6 or more markers are present selected from the group consisting of marker mME15248, mME17306, mME26059, mME38048, mME21974 and/or mME12777 and/or any marker in between any pair of of these markers, such as markers of group cc), dd), ee), ff) and/or gg) supra.

In another embodiment the presence of the introgression fragment, or the chromosome 11 region (or orthologous chromosome 11 region), comprising the Wf_11.1 resistance locus, is detectable by a molecular marker assay which detects at least one of the following markers:
i) the CC genotype or CT genotype for the SNP marker mME15248 in SEQ ID NO: 3;

ii) the CC genotype or CT genotype for SNP marker mME17306 in SEQ ID NO: 4;
iii) the AA genotype or AT genotype for SNP marker mME26059 in SEQ ID NO: 5;
iv) the GG genotype or GA genotype for SNP marker mME38084 in SEQ ID NO: 6;
v) the CC or AC genotype for SNP marker mME21974 in SEQ ID NO: 7;
vi) the CC genotype or CT genotype for SNP marker mME12777 in SEQ ID NO: 8;
vii) any wild melon or wild relative of melon genome specific marker in-between marker mME17490 and marker mME12777.

In one aspect, at least two, at least three, at least four or more markers are detected from the markers above. Specifically, at least two, at least three, at least four or more (e.g. all) of markers i) to vi) are detected.

In one aspect the markers in between marker mME17490 and marker mME12777 are one or more markers selected from the group: the (resistance genotype of) SNP marker mME22724; the (resistance genotype of) SNP marker mME21134; and the (resistance genotype of) SNP marker mME17011.

The molecular markers described herein may be detected according to standard method. For example SNP markers can easily be detected using a KASP-assay (see www.kp-bioscience.co.uk) or other assays. For developing the KASP-assay 70 base pairs upstream and 70 basepairs downstream of the SNP are selected and two allele-specific forward primers and one allele specific reverse primer is designed. See e.g. Allen et al. 2011, Plant Biotechnology J. 9, 1086-1099, especially p 1097-1098 for KASP assay method.

Thus, in one aspect, the SNP markers and the presence/absence of the marker associated with the Wf_11.1-resistance allele is determined using a KASP assay (e.g. as described in the Examples), but equally other assays can be used. For example, optionally DNA sequencing may also be used.

Physical mapping using BACs (Bacterial Artificial Chromosomes) and development of markers for the BACs can be carried out to map the physical location of Wf_11.1 on chromosome 11 and to develop markers which lie physically between any of the markers mentioned and to determine physical distances between markers and/or determine introgression size.

The size of an introgression fragment can for example also be determined by visualization of the introgression using Fluorescent in situ hybridization (FISH) images (Verlaan et al. 2011, Plant Journal 68: 1093-1103).

In one embodiment of the invention, the Wf-resistance conferring introgression fragment is equal to or less than 20 Mb in size, equal to or less than 10 Mb in size, preferably equal to or less than 8 Mb in size, equal to or less than 7, 6, 5, 4, 3, 2 or 1 Mb in size, more preferably even less, such as equal to or less than 500 kb, 400 kb, 300 kb, 200 kb, 100 kb, 50 kb, 25 kb, 20 kb, 15 kb, or less, but still comprises the Wf-resistance allele and still confers whitefly resistance to an otherwise susceptible *C. melo* plant. Resistance is conferred by the recombinant chromosome 11, and the introgression fragment comprising the Wf resistance allele when the introgression fragment is in heterozygous or homozygous form. Plants with smaller introgression fragments on chromosome 11 can be generated by generating new recombinant plants from a population of plants derived from a cross between a cultivated whitefly susceptible plant and a wild whitefly resistant melon or relative of melon. Alternatively, when a cultivated *C. melo* plant having a whitefly-resistance conferring introgression fragment is identified, the introgression size can be reduced by e.g. selfing that plant and selecting recombinant progeny having smaller introgression sizes.

In tomato, for example the large *S. chilense* introgression fragment on chromosome 6 (about 27 cM) which comprises the Ty-3 allele has been reduced by selecting a recombinant progeny line (LA1931-AL-F2), which comprises a much smaller *S. chilense* introgression fragment (about 6 cM) comprising Ty-3 (see Ji et al. 2007, Mol. Breeding 20: 271-284).

The cultivated melon plant according to the invention may be an inbred or an F1 hybrid. In one aspect the F1 hybrid comprises the introgression fragment in heterozygous form, i.e. produced by crossing two inbred parent lines, one of which possesses the introgression fragment (preferably in homozygous form, although not necessarily) and collecting the F1 hybrid seeds from said cross. The F1 hybrid may also comprise the introgression fragment in homozygous form, i.e. produced by crossing two inbred parent lines, each comprising the introgression fragment in homozygous or heterozygous form.

The cultivated melon plant may be of any type. Preferably it has good agronomic and good fruit quality characteristics, such as large average fruit weight (at least 500 g, 600 g, 700 g, 800 g, 900 g, 1000 g or more), high average brix of the fruits (e.g. an average refractometer % total soluble solids of at least 9%, 10%, 11%, 12%, 13%, 14%, 16%, 18% or more), many fruits being produced per plant, firm fruit flesh, etc. The cultivated melon may be a *C. melo cantalupensis, C. melo inodorous* and *C. melo reticulatus. C. melo cantalupensis* are also referred to as Canteloupes and are primarily round in shape with prominent ribs and almost no netting. Most have orange, sweet flesh and they are usually very fragrant. In contrast to the European cantaloupe, the North American 'Cantaloupe' is not of this type, but belongs to the true muskmelons. *C. melo inodorous* (or winter melons) can be subdivided into different types, such as Honeydew melon, Piel de Sapo, Sugar melon, Japanese melon, etc. *C. melo reticulatus* is the true muskmelon, with reticulated skin (netted) and includes Galia melons, Sharlyn melons and the North American cantaloupe. Melons come in many sizes and shapes including round, oval, and cylindrical. The flesh is generally orange and quite sweet, but some varieties of melon and specifically, the Persian melons, can have green or white flesh. Some green-fleshed melons are quite sweet, but most of the green- and white-fleshed melons have a less sweet, but very refreshing flavor. Melons according to the invention may be any type, e.g. any of the here mentioned types. E.g. in one aspect the Wf resistant melon is a Yellow Canary; in another aspect a cantaloupe.

Also other resistances may be introduced into the melon plants of the invention, such as resistance to one or more of the following diseases: MYaV resistance (Melon Yellowing Associated Virus); Bacterial Wilt, Root Rot, Crown Blight, Melon Rust, Powdery Mildew, *Verticillum* Wilt, Sulphur Burn, Scab, Watermelon Mosaic, Downy Mildew, *Fusarium oxysporum* f.sp. *melonis* (Fom) race 0, *Fusarium oxysporum* f.sp. *melonis* (Fom) race 1, *Fusarium oxysporum* f.sp. *melonis* (Fom) race 2, *Fusarium oxysporum* f.sp. *melonis* (Fom) race 1.2, *Fusarium* Wilt R2, Root Knot (Nematode), Anthracnose, Cucumber Mosiac, and Squash Mosaic, and/or resistance to one or more of the following pests: Aphid resistance, Pickle Worm, Darkling Ground Beetle, Banded Cucumber Beetle, Mite, Western Spotted Cucumber Beetle, Melon Leafhopper, Melon Worm, Western Striped Cucumber Beetle or Melon Leafminer. Other resistance genes, against pathogenic viruses, fungi, bacteria or pests may also be introduced. In one aspect also ZYMV and/or WMV (Zuccini Yellow Mozaic Virus/Watermelon Mosaic Virus) resistance may be introduced into plants comprising the Wf_11.1 QTL, e.g. such as the QTL described in WO2014/031770, which QTL is at a different locus of chromosome 11 than the Wf 11.1 locus.

In one aspect seeds from which plants of the invention can be grown are provided. In one aspect the seeds are F1 hybrid seeds, which comprise the recombinant chromosome 11 in homozygous or heterozygous form and which have a whitefly-resistance phenotype when grown in the field.

Also containers and packages containing or comprising seeds from which plants of the invention can be grown are provided herein. These may be labelled as containing cultivated melon seeds having whitefly resistance.

Also progeny seeds and progeny plants of plants of the invention are provided, which retain the whitefly resistance conferring introgression on chromosome 11, or a smaller introgression, i.e. a resistance conferring part of the introgression fragment. Progeny may be any generation obtained by selfing a melon plant according to the invention and/or crossing a melon plant according to the invention with another melon plant one or more times. Progeny are, therefore, either the generation (seeds) produced from the first cross (F1) or selfing (S1), or any further generation produced by crossing and/or selfing (F2, F3, etc.) and/or backcrossing (BC1, BC2, BC1S1, etc.) one or more selected plants of the F1 and/or S1 and/or BC1 generation (or plants of any further generation, e.g. the F2) with another melon plant (and/or with a wild relative of melon). Progeny are preferably selected to retain the recombinant chromosome 11 comprising the introgression fragment from wild melon or from a wild relative of melon. Thus progeny also have the whitefly-resistance phenotype, preferably the same level of whitefly resistance as the plant used in the initial cross or selfing. The presence of (or retention of) the introgression fragment comprising the QTL Wf_11.1 can be determined in the whitefly-resistance assay, phenotypically, and/or the molecular marker assay(s) described herein. Regarding phenotypic assessment, of course consideration needs to be given to the dominant nature of the Wf-resistance allele.

In a further aspect parts of the melon plants according to the invention are provided. Parts include for example cells and cell-cultures, tissue cultures, vegetative plant tissues (leaves, roots, etc.), flowers, pollen, embryos, fruits, parts of fruits, etc. The plant parts comprise the introgression fragment on chromosome 11, as described, and as can be detected using one or more of the marker assays described. Also, when whole plants are regenerated from such melon parts, such as cells, cell- or tissue cultures, the regenerated plants comprise the recombinant chromosome 11, and the whitefly resistance phenotype.

Thus, also provided is a plant cell, tissue or plant part of a plant or of a seed according the invention comprising at least one recombinant chromosome 11, wherein said recombinant chromosome 11 comprises an introgression fragment from a wild C. melo plant and wherein said introgression fragment comprises an allele conferring whitefly resistance.

Also in vitro cell cultures and in vitro tissue cultures are encompassed herein, of cells or tissues comprising a recombinant chromosome 11 described. Preferably the cells or tissues can be regenerated into a whole melon plant, i.e. the cells are regenerable cells and the tissues comprise regenerable cells. Thus, also vegetative propagations of the plants according to the invention are an embodiment herein. Thus, a vegetatively propagated cultivated melon plant is provided which comprises the whitefly resistance phenotype and a recombinant chromosome 11 as described herein.

In a specific aspect a melon fruit harvested from a plant according to the invention is provided. Marketable melon fruits are generally sorted by size and quality after harvest. Also containers or packages comprising or consisting of harvested melon fruits are provided. Again, the cells of the fruits (such as cells of the fruit, e.g. exocarp, endocarp, fruit flesh, columnella) are distinguishable from other melons by the presence of the recombinant chromosome 11 (as determinable in one or more of the molecular marker assays and/or in a whitefly resistance assay by e.g. growing the seeds present in the fruits, or progeny obtained by selfing the plants grown from the seeds).

The invention also provides for a food or feed product comprising or consisting of a plant part described herein, the plant part comprising at least one recombinant chromosome 11, wherein said recombinant chromosome 11 comprises an introgression fragment from a wild C. melo plant and wherein said introgression fragment comprises an allele conferring whitefly resistance. Preferably the plant part is a melon fruit or part thereof and/or an extract from a plant part described herein. The food or feed product may be fresh or processed, e.g., canned, steamed, boiled, fried, blanched and/or frozen, etc. For example, containers such as cans, boxes, crates, bags, cartons, Modified Atmosphere Packagings, films (e.g. biodegradable films), etc. comprising plant parts such as fruits or fruit parts (fresh and/or processed) described herein are also provided herein.

Methods and Uses According to the Invention

In a further embodiment, the invention provides for a method of producing a new cultivated melon plant which comprises an introgression fragment which confers whitefly-resistance when in homozygous or heterozygous form, as described. The method comprises crossing a plant of the invention, or a progeny plant thereof, either as male or as female parent, with a second melon plant (or a wild relative of melon) one or more times, and/or selfing a melon plant according to the invention, or a progeny plant thereof, one or more times, and selecting progeny from said crossing and/or selfing. The first and/or the second melon plant may for example be a line or variety of the species C. melo cantalupensis, C. melo inodorous or C. melo reticulatus.

Thus, a method for transferring the recombinant chromosome 11, comprising the whitefly-resistance conferring locus (Wf_11.1), from one (cultivated) melon plant into another (cultivated) melon plant is provided, especially into whitefly-susceptible melon varieties or breeding lines.

The method comprises the steps of:
a) providing a first melon plant comprising at least one recombinant chromosome 11 having an introgression fragment comprising an allele conferring whitefly resistance, preferably in homozygous form,
b) providing a second melon plant, especially a whitefly susceptible melon plant,
c) crossing said melon plant of a) with said melon plant of b),
d) collecting F1 hybrid seeds from said cross, and optionally
e) selfing the plant grown from said F1 hybrid seeds to produce F2 seeds, and optionally selecting the F2 seeds having the recombinant chromosome 11, and optionally
f) breeding further with plants grown from said F2 seeds to produce a melon plant having good agronomic characteristics and comprising the introgression fragment in homozygous or heterozygous form.

The presence or absence of the recombinant chromosome 11, and of the introgression fragment, may be determined by one or more of the molecular marker assays described herein and/or by (a) whitefly-resistance assay(s). Further breeding in step f) may comprise selfing, crossing, double haploid production, backcrossing, etc. Plants and seeds obtainable by the above method are encompassed herein.

Thus the presence of the resistance genotype of one or more markers of the groups and/or subgroups described in a) to zzz) above is indicative of the presence of the introgression fragment. In particular the presence of the resistance genotype of one or more markers selected from the group: mME20364, mME17490, mME15248, mME17306 mME26059, mME38084, mME21974, mME12777, mME15151, mME26139, mME48762 mME2503, mME40109, any wild melon or wild-relative of melon genome-specific marker as listed in the groups and/or subgroups of a) to zzz) above, and any wild melon or wild relative of melon genome specific marker in-between the marker mME20364 and the marker mME40109. Any of these single markers, groups or subgroups of markers are referred to when reference is made herein to the "markers described elsewhere herein" or "molecular marker assays described herein".

Also provided is a method of producing *C. melo* F1 hybrid plants comprising a whitefly resistance phenotype comprising:
a) providing a first inbred melon plant comprising at least one recombinant chromosome 11 having an introgression fragment comprising an allele conferring whitefly resistance,
b) providing a second inbred melon plant with or without recombinant chromosome 11 having an introgression fragment comprising an allele conferring whitefly resistance,
c) crossing said melon plant of a) with said melon plant of b),
d) collecting F1 hybrid seeds from said cross.

The inbred melon plant of a) and b) may be homozygous and/or heterozygous for the introgression fragment, and they may contain introgression fragments of different sizes and/or of different origin, i.e. from different wild melons or wild relatives of melon.

The F1 hybrid seeds preferably comprise at least one recombinant chromosome 11 and the F1 plants grown from the seeds are therefore whitefly resistant in their phenotype.

The presence or absence of the recombinant chromosome 11, and of the introgression fragment, may be determined by one or more of the molecular marker assays described herein and/or by (a) whitefly-resistance assay(s). Plants and seeds obtainable by the above method are encompassed herein.

In a different aspect a method for producing a cultivated *C. melo* plant comprising an introgression fragment on chromosome 11, wherein said introgression fragment comprises a whitefly-resistance allele, is provided, said method comprising the steps:
a) providing a first cultivated melon plant being susceptible to whitefly,
b) providing a second wild melon plant being resistance to whitefly,
c) crossing said melon plant of a) with said melon plant of b),
d) collecting F1 seeds from said cross and backcrossing an F1 plant to the melon plant of a) to produce a backcross (BC1) population, or selfing said F1 plants one or more times to produce an F2 or F3 or higher generation selfing population,
e) optionally backcrossing a plant of d) one or more times to the melon plant of a) to produce a higher generation backcross population, and
f) identifying a F2, F3, or higher generation selfing, or BC1 or higher generation backcross plant which comprises an introgression on chromosome 11, wherein said introgression fragment comprises a whitefly-resistance allele.

When referring to backcross populations in the method, the backcross populations may also be selfed, i.e. BC1S1, BC1S2, BC2S1, BC2S2, or others.

In one or more of steps b) to f) the presence of the whitefly-resistance allele (or the introgression fragment or wild chromosome 11 region comprising the allele) may be tested (and plants may be selected) by carrying out a molecular marker assay as described elsewhere herein, e.g. by determining whether the plant comprises the resistance genotype of one or more of the markers linked to the QTL, as described.

Using this method, one can generate and/or select new cultivated melon plants comprising an introgression with QTL Wf_11.1 from a wild source, such as a wild melon or wild relative of melon (such as from NCIMB 41965 or NCIMB 41966, or other wild melons or wild relatives of melon).

In one aspect the method for producing a cultivated *C. melo* plant comprising an introgression fragment on chromosome 11, wherein said introgression fragment comprises a whitefly-resistance allele, comprises the steps:
a) providing a first cultivated melon plant being susceptible to whitefly,
b) providing a second wild melon plant being resistance to whitefly,
c) crossing said melon plant of a) with said melon plant of b),
d) collecting F1 seeds from said cross and backcrossing an F1 plant to the melon plant of a) to produce a backcross (BC1) population, or selfing said F1 plants one or more times to produce an F2 or F3 population,
e) optionally selfing the backcross population to produce e.g. a BC1S1 or BC1S2 population,
f) identifying a F2, F3, BC1 BC1S1, or BC1S2 plant which comprises the resistance genotype for one or more of the SNP markers described previously.

Also provided is a method for identifying a wild melon plant comprising whitefly resistance on chromosome 11, said method comprising:
a) providing a wild melon accession or several wild melon accessions;
b) screening said wild melon accession(s) using a molecular marker assay which detects at least one (or more) markers described elsewhere herein; and
c) identifying and/or selecting a wild melon plant comprising the resistance genotype of at least one (or more) of the markers described elsewhere herein; and optionally
d) confirming whitefly resistance in a whitefly resistance assay; and optionally
e) introgressing said whitefly resistance from said wild accession into cultivated melon.

In step c) also other molecular marker tests described elsewhere herein can be used. With this method one can, thus, screen wild melon accessions or wild relatives of melon for the presence of one or more of the markers and, thus, the presence of QTL Wf_11.1 and introgress the resistance-conferring part of these new resistance sources into cultivated, whitefly-susceptible, melon plants. Plants and seeds obtained by this method are also an embodiment of the invention.

Thus, for example, a method for identifying a wild melon plant comprising whitefly resistance on chromosome 11 comprising the steps:

A) providing a wild melon accession or several wild melon accessions;
B) screening said wild melon accession(s) using a molecular marker assay which detects at least one SNP marker selected from the group consisting of:
   a) the CC genotype or CT genotype for the SNP marker mME20364 in SEQ ID NO: 1;
   b) the AA genotype or AG genotype for the SNP marker mME17490 in SEQ ID NO: 2;
   c) the CC genotype or CT genotype for the SNP marker mME15248 in SEQ ID NO: 3;
   d) the CC genotype or CT genotype for SNP marker mME17306 in SEQ ID NO: 4;
   e) the AA genotype or AT genotype for SNP marker mME26059 in SEQ ID NO: 5;
   f) the GG genotype or GA genotype for SNP marker mME38084 in SEQ ID NO: 6;
   g) the CC or AC genotype for SNP marker mME21974 in SEQ ID NO: 7;
   h) the CC genotype or CT genotype for SNP marker mME12777 in SEQ ID NO: 8;
   i) the GG genotype or GA genotype for SNP marker mME15151 in SEQ ID NO: 9;
   j) the CC genotype or CA genotype for SNP marker mME26139 in SEQ ID NO: 10;
   k) the CC genotype or CA genotype for SNP marker mME48762 in SEQ ID NO: 11;
   l) the CC genotype or CT genotype for SNP marker mME25039 in SEQ ID NO: 12;
   m) the TT genotype or TC genotype for SNP marker mME40109 in SEQ ID NO: 13;
   or any wild melon or wild relative of melon genome specific marker in-between the marker of a) and the marker of m);
C) identifying and/or selecting a wild melon plant comprising at least one, two, three or more of said SNP markers and
D) confirming whitefly resistance of said wild melon plant in a whitefly resistance assay; and optionally
E) introgressing said whitefly resistance from said wild accession into cultivated melon.

Alternatively, a method for identifying a wild melon plant comprising whitefly resistance on chromosome 11, comprises the following steps:

A) providing a wild melon accession or several wild melon accessions;
B) testing whitefly resistance of said wild melon accessions in a whitefly resistance assay;
C) screening said wild melon accession(s) using a molecular marker assay which detects at least one SNP marker selected from the group consisting of:
   a) the CC genotype or CT genotype for the SNP marker mME20364 in SEQ ID NO: 1;
   b) the AA genotype or AG genotype for the SNP marker mME17490 in SEQ ID NO: 2;
   c) the CC genotype or CT genotype for the SNP marker mME15248 in SEQ ID NO: 3; d) the CC genotype or CT genotype for SNP marker mME17306 in SEQ ID NO: 4;
   e) the AA genotype or AT genotype for SNP marker mME26059 in SEQ ID NO: 5;
   f) the GG genotype or GA genotype for SNP marker mME38084 in SEQ ID NO: 6;
   g) the CC or AC genotype for SNP marker mME21974 in SEQ ID NO: 7;
   h) the CC genotype or CT genotype for SNP marker mME12777 in SEQ ID NO: 8;
   i) the GG genotype or GA genotype for SNP marker mME15151 in SEQ ID NO: 9;
   j) the CC genotype or CA genotype for SNP marker mME26139 in SEQ ID NO: 10;
   k) the CC genotype or CA genotype for SNP marker mME48762 in SEQ ID NO: 11;
   l) the CC genotype or CT genotype for SNP marker mME25039 in SEQ ID NO: 12;
   m) the TT genotype or TC genotype for SNP marker mME40109 in SEQ ID NO: 13;
   or any wild melon or wild relative of melon genome specific marker in-between the marker of a) and the marker of m);
D) identifying and/or selecting a wild melon plant comprising whitefly resistance and comprising at least one, two, three or more of said SNP markers, and optionally
E) introgressing said whitefly resistance from said wild accession into cultivated melon.

Also provided is a cultivated melon plant produced by the methods above, which plant comprises resistance against whitefly, wherein said resistance is conferred by an introgression fragment on chromosome 11 in homozygous or heterozygous form.

In still another aspect a method for identifying a cultivated *C. melo* plant comprising an introgression fragment on chromosome 11, wherein said introgression fragment comprises a whitefly-resistance allele, is provided, said method comprising:

a) providing a population of recombinant, cultivated *C. melo* plants (such as an F2, F3, or higher generation selfing, BC1, BC2, BC1S1 or higher generation backcross population),
b) screening said population using a molecular marker assay which detects at least one (or more) marker(s) described elsewhere herein; and
c) identifying and/or selecting a plant comprising the resistance genotype of one or more of the markers described elsewhere herein.

Thus, for example in one aspect a method for identifying a cultivated *C. melo* plant comprising an introgression fragment on chromosome 11 is provided, wherein said introgression fragment comprises an whitefly resistance allele, comprising:

a) providing a population of recombinant, cultivated *C. melo* plants (such as an F2, F3, BC1, BC2, BC1S1 population),
b) screening said population using a molecular marker assay which detects at least one SNP marker selected from the group consisting of: mME15248, mME17306, mME26059, mME38084, mME21974, mME12777; and
c) identifying and/or selecting a plant comprising
   i) the CC or CT genotype for the SNP marker mME15248 in SEQ ID NO: 3; and/or
   ii) the CC or CT genotype for SNP marker mME17306 in SEQ ID NO: 4; and/or
   iii) the AA or AT genotype for SNP marker mME26059 in SEQ ID NO: 5; and/or
   iv) the GG or GA genotype for SNP marker mME38084 in SEQ ID NO: 6; and/or
   v) the CC or CA genotype for SNP marker mME21974 in SEQ ID NO: 7; and/or
   vi) the CC or CT genotype for SNP marker mME12777 in SEQ ID NO: 8; and/or vii) any wild melon or wild relative of melon genome specific marker in-between marker mME17490 and marker mME12777.

In this method also other molecular marker tests described elsewhere herein can be used. Thus, using this method one can detect the presence of an introgression fragment on chromosome 11 comprising QTL Wf_11.1 in cultivated melon plants or plant parts.

In yet another aspect a method for detecting whether a cultivated C. melo plant comprises an introgression fragment on chromosome 11, wherein said introgression fragment comprises a whitefly-resistance allele, is provided, said method comprising:
a) providing cultivated C. melo plant,
b) screening said plant using a molecular marker assay which detects at least one (or more) marker(s) described elsewhere herein.

Molecular marker screening obviously involves obtaining plant material and analyzing the genomic DNA of the material for the marker genotype.

In this method also other molecular marker tests described elsewhere herein can be used. Thus, using this method one can detect the presence of an introgression fragment on chromosome 11 comprising QTL Wf_11.1 in cultivated melon plants or plant parts. If one or more of the markers which are linked to the QTL are present, one can conclude that the plant comprises a whitefly-resistance conferring introgression fragment on chromosome 11.

One can also use the methods and the markers described herein to reduce the size of the wild introgression fragment comprising the QTL Wf_11.1, i.e. to generate and select recombinants having a smaller introgression fragment on chromosome 11, but which retain the whitefly resistance conferring part of the introgression fragment. One can equally develop alternative molecular markers linked to Wf_11.1 for use in any of the aforementioned methods.

In one aspect the invention encompasses the use of a recombinant chromosome 11 comprising an introgression fragment from a wild C. melo plant, said introgression fragment comprising an allele conferring whitefly-resistance, for breeding melon varieties having whitefly resistance.

In one aspect the invention encompasses the use of a recombinant chromosome 11 comprising an introgression fragment from a wild C. melo plant, said introgression fragment comprising an allele conferring whitefly-resistance, for breeding melon varieties having whitefly resistance, wherein said recombinant chromosomes 11 is the recombinant chromosome 11 as found in seeds deposited under accession number NCIMB 42221 or NCIMB42220, or is derived from said recombinant chromosome 11. Thus, in one aspect a cultivated melon plant according to the invention comprising a recombinant chromosome 11 obtained by (obtainable by) crossing a plant grown from seeds deposited under accession number NCIMB 42221, or NCIMB 42220, or from progeny thereof which retain the recombinant chromosome 11, with another melon plant.

DNA and Chromosomes According to the Invention

In one aspect a modified (recombinant) cultivated C. melo chromosome 11 is provided herein, which comprises an introgression fragment of a wild melon or wild relative of melon, as described throughout the specification. In one aspect the recombinant chromosome 11 is isolated from its natural environment. In another aspect it is in a plant cell, especially in a melon cell, especially in a cultivated C. melo cell. Also an isolated part of the recombinant chromosome 11 comprising the whitefly resistance allele is provided herein.

In a further aspect a recombinant nucleic acid molecule, especially a recombinant DNA molecule, is provided which comprises a whitefly resistance-allele according to the invention. In one aspect the whitefly resistance allele is detectable by one or more of the molecular marker assays described herein. Also a DNA vector is provided comprising the recombinant DNA. The recombinant DNA molecule or DNA vector may be an isolated nucleic acid molecule. The DNA comprising the whitefly resistance allele may be in a microorgansims, such as a bacterium (e.g. Agrobacterium).

The use of such a (isolated or extracted) nucleic acid molecule and/or of such a recombinant chromosome 11 or part thereof for generating plant cells and plants comprising a whitefly resistance allele is encompassed herein. In one aspect it may be used to generate transgenic melon cells, melon plants and melon parts (e.g. fruits) comprising the whitefly resistance allele and the plant comprises an whitefly resistance phenotype.

Thus, transgenic plant cells, e.g. transgenic melon cells, comprising in their genome a recombinant chromosome 11 as described and/or a recombinant nucleic acid molecule comprising a whitefly resistance allele are also an embodiment of the invention. In one aspect the DNA molecule comprising the whitefly resistance allele is stably integrated into the melon genome.

The whitefly resistance allele may also be cloned and a chimeric gene may be made, e.g. operably linking a plant expressible promoter to the whitefly resistance allele. Such a chimeric gene may be introduced into a plant cell and the plant cell may be regenerated into a whole plant to produce a transgenic plant. In one aspect the transgenic plant is a melon plant.

Thus, transgenic plants, especially transgenic cultivated melon plants, comprising whitefly resistance allele and having a whitefly resistance phenotype are provided herein.

Especially cells or cell cultures comprising a recombinant chromosome 11 according to the invention are an embodiment, independent whether the recombinant chromosome 11 is introduced by transgenic methods or by breeding methods. The cells are e.g. in vitro and are regenerable into melon plants comprising the recombinant chromosome 11 of the invention.

Also the molecular marker sequences (and isolated nucleic acid molecules comprising the sequence) disclosed herein and molecular markers in between any of the mentioned molecular markers described herein and depicted in FIG. 1, linked to the whitefly resistance conferring QTL, Wf_11.1, and their use in detecting and/or generating whitefly resistant melon plants are encompassed herein.

FIGURE LEGENDS

FIG. 1: The LOD profile of Wf_11.1, a QTL on melon Chr11 conferring resistance to whitefly (Bemisia tabaci biotype B). The Chr. 11 linkage maps of two crosses (MA 17115)-Q-1-4×NCIMB41965 and [(990631-2)-Q-1-K× NCIMB41966 are represented by solid bars, and SNP markers are to the right and left sides of the bars, respectively, and genetic distance in cM in parenthesis. Common SNP markers between the two maps are indicated with connecting lines. The peak LOD for (MA 17115)-Q-1-4×NCIMB41965 and (990631-2)-Q-1-K×NCIMB41966 was 12.76 and 8.25, explaining 57.9% and 49.7% of observed variation, respectively. Dashed lines show significant LOD threshold at P=0.05. Hatched bars to either side of the maps show Wf_11.1 QTL introgression in the $F_3$ recombinants (from H11_5008-0511 and H11_5007-0205 $F_2$ progenitors) for which seed deposits were made under accession number NCIMB 42221 and NCIMB 42220, respectively. These contain the QTL Wf_11.1 in homozygous form.

Figure 2:
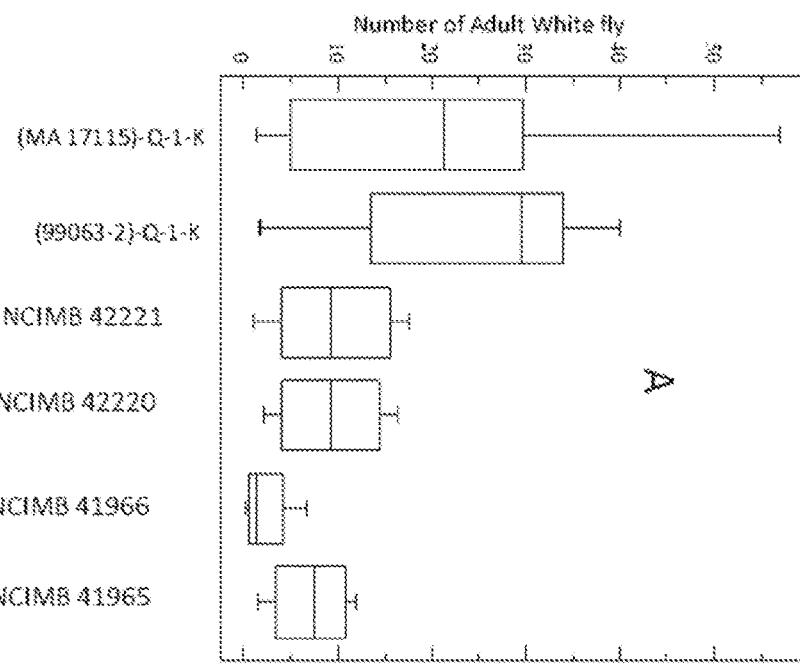
Figure 2:
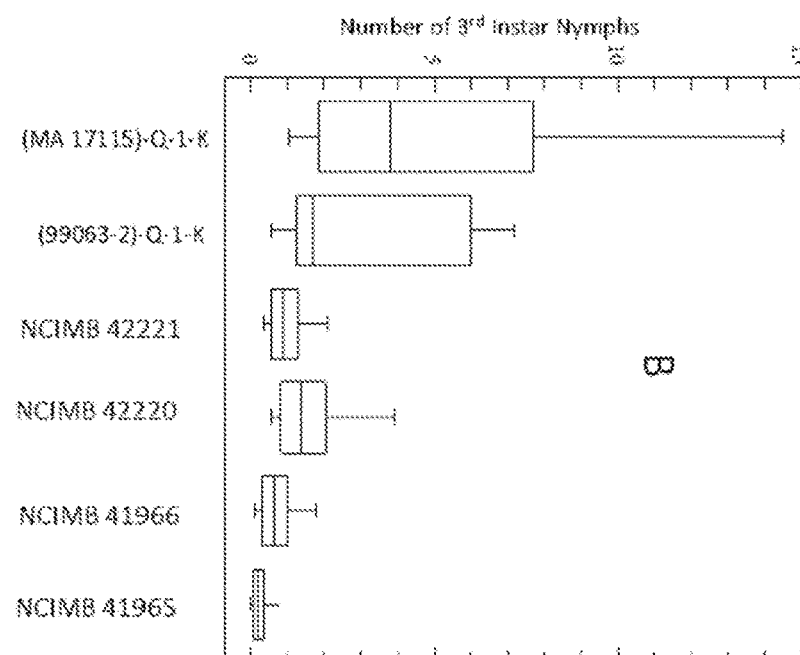

FIG. 2: Boxplot of (average) number of adult whitefly and $3^{rd}$ instar nymphs from field evaluation of two $F_4$ plant lines (selfings of NCIMB 42221 and NCIMB 42220), two resistant mapping parents (NCIMB 41965 and NCIMB 41966) and two susceptible mapping parents ((MA 17115)-Q-1-4, which is a whitefly susceptible cantaloupe breeding line and (99063-2)-Q-1-K, which as a whitefly susceptible canary breeding line).

Seed Deposits

A representative sample of seeds of wild melon accessions comprising the QTL (designated Wf_11.1) for whitefly resistance on chromosome 11 were deposited by Nunhems B.V. on 2 May 2012 at the NCIMB Ltd. (Ferguson Building, Craibstone Estate, Bucksburn Aberdeen, Scotland AB21 9YA, UK) according to the Budapest Treaty, under the Expert Solution (EPC 2000, Rule 32(1)). Seeds were given the following deposit numbers: NCIMB 41965 and NCIMB 41966.

Representative sample of seeds of cultivated melon plants comprising the QTL for whitefly resistance on chromosome 11 in homozygous form (designated Wf_11.1) was deposited by Nunhems B.V. on 19 Feb. 2014 at the NCIMB Ltd. (Ferguson Building, Craibstone Estate, Bucksburn Aberdeen, Scotland AB21 9YA, UK) according to the Budapest Treaty, under the Expert Solution (EPC 2000, Rule 32(1)). Seeds were given the following deposit number: NCIMB 42221 and NCIMB 42220.

The Applicant requests that samples of the biological material and any material derived therefrom be only released to a designated Expert in accordance with Rule 32(1) EPC or related legislation of countries or treaties having similar rules and regulation, until the mention of the grant of the patent, or for 20 years from the date of filing if the application is refused, withdrawn or deemed to be withdrawn.

Access to the deposit will be available during the pendency of this application to persons determined by the Director of the U.S. Patent Office to be entitled thereto upon request. Subject to 37 C.F.R. § 1.808(b), all restrictions imposed by the depositor on the availability to the public of the deposited material will be irrevocably removed upon the granting of the patent. The deposit will be maintained for a period of 30 years, or 5 years after the most recent request, or for the enforceable life of the patent whichever is longer, and will be replaced if it ever becomes nonviable during that period. Applicant does not waive any rights granted under this patent on this application or under the Plant Variety Protection Act (7 USC 2321 et seq.).

The following non-limiting Examples describe how one can obtain plants according to the invention, comprising a recombinant chromosome 11. Unless stated otherwise in the Examples, all recombinant DNA techniques are carried out according to standard protocols as described in Sambrook et al. (1989) *Molecular Cloning: A Laboratory Manual*, Second Edition, Cold Spring Harbor Laboratory Press, and Sambrook and Russell (2001) *Molecular Cloning: A Laboratory Manual*, Third Edition, Cold Spring Harbor Laboratory Press, NY; and in Volumes 1 and 2 of Ausubel et al. (1994) *Current Protocols in Molecular Biology, Current Protocols*, USA. Standard materials and methods for plant molecular work are described in *Plant Molecular Biology Labfax* (1993) by R. D. D. Croy, jointly published by BIOS Scientific Publications Ltd (UK) and Blackwell Scientific Publications, UK. Standard breeding methods are described in 'Principles of Plant breeding', Second Edition, Robert W. Allard (ISBN 0-471-02309-4).

Example 1—Resistance on Chromosome 11 of NCIMB 41965 and NCIMB 41966

Material and Methods

Several melon accessions were screened in Spain for white fly resistance under natural insect infestation. Two accessions were identified as being resistant, seeds of which were deposited under accession numbers NCIMB 41965 and NCIMB 41966.

Two bi-parental mapping populations were developed from these two resistant sources. The first population was a cross between a white fly susceptible cantaloupe breeding line ((MA17115)-Q-1-4) and the resistant accession NCIMB 41965 and the second was a cross between a canary breeding line ((990631-2)-Q-1-K and the resistant accession NCIMB41966. $F_2$ populations were used for linkage mapping, and phenotyping for white fly resistance was done on $F_3$ families.

$F_3$ families were phenotyped in an insect-proof net house in 2011 with appropriate susceptible controls (susceptible parent lines, and Medellin F1 and Caribbean Gold F1). Plants were maintained in pots, free of other insects and without insecticide. Each $F_3$ family was planted in four replicates with three plants/replicate/$F_3$ family in a randomized complete block design (RCBD). Fifteen days old plants were transferred to white fly chamber and exposed to whitefly infestation for 7 days after which they were transferred back to insect-free net house. Seven days (+4 days, depending on temperature) after withdrawal from whitefly chamber, the third or fourth leaf was selected from each test plant. Five leaf discs (1.5 cm diameter) were taken randomly from each leaf, and third instar whitefly nymphs (pink colored eye) were counted under stereomicroscope. Over the period of the experiment, temperature fluctuation was 25° C.-34° C.

Another round of phenotyping was conducted in 2012 on $F_3$ recombinants. These $F_3$ recombinants were progeny of selection from large $F_2$ populations of both crosses (1,400 $F_2$ individuals per cross) based on SNP markers spanning the QTL region. The same experimental design (RCBD) and scoring scale were applied as in 2011. Some $F_3$ individuals were selected based on resistance scores, tissue sampled and genotyped with QTL markers to fine-map the resistance QTL.

From the 2012 screening, resistant $F_3$ recombinants carrying the QTL interval were selfed and their $F_4$ families were planted in Spain in 2013 for field evaluation (free choice). The resistant and susceptible parents of both crosses were included in the field evaluation. Experimental lay out was RCBD with three replicates and three plants per replicate. Plants were transplanted to the field 30 days after sowing. Observations were made 7, 14, 21, 28 and 35 days after transplanting (DAT). Adults white flies were counted 7, 14 and 21 DAT while third and fourth instar nymphs were counted 14, 21, 28 and 35 DAT. Counting of instar was done on 5 leaf discs per plant. Analysis of variance (ANOVA) was conducted for test of significance among the genotypes. Seed deposits were made for $F_3$ recombinants (H11_5008-0511 and H11_5007-0205), which have been given Accession numbers NCIMB 42221 and NCIMB 42220, respectively.

Genotyping of the F$_2$ populations was conducted on a proprietary single nucleotide polymorphism (SNP) platform containing 4,600 SNPs. For each population, 96 individuals were analyzed. Linkage mapping was conducted with Join-Map 4. Several ICuGI SSR (Single Sequence Repeat) and SNP markers from Deleu et al. (2012—*BMC Plant Biology* 2009, 9:90) map were used as anchor markers for the assignment of chromosome number and map orientation of linkage groups. Genotyping of subsequent populations (large F$_2$ population and F$_3$ recombinants) was done using KASPar assays designed for polymorphic SNPs. QTL analyses were conducted with MapQTL 5. Significant LOD threshold was determined by genome wide permutation with 1000 iterations.

Results

For both mapping populations linkage mapping analyses showed twelve linkage groups, corresponding to the haploid chromosome number of melon.

QTL analyses using phenotype data from replicated F$_3$ families showed a QTL for resistance to whitefly (Wf_11.1) on Chr11 from both mapping populations.

The peak LODs were 8.2 and 12.76, and variation explained were 49.7% and 57.9% for population (990631-2)-Q-1-K×NCIMB 41966 and population (MA17115)-Q-1-4×NCIMB 41965, respectively (FIG. 1).

Thirteen SNP markers were found to be common for the Wf_11.1 QTL in both mapping populations, as listed herein below in Table 1 and shown in FIG. 1:

TABLE 1-A

| Marker | SNP | Resistance genotype | SEQ ID | Sequence comprising SNP |
|---|---|---|---|---|
| mME20364 | [C/T] | CC | 1 | TAAGGGTTGGTTACGCAAGGGTCGACTTTCAATC TGTTTGAGAAAACAAG[C/T]GGTTCTTAGCTMTTG ACCTTTATGATAGGTGCCTTGAGAAGGGCCCTCR T |
| mME17490 | [A/G] | AA | 2 | GCATTTTTACAGCATAGAAAAACTATGGTCGGGC [A/G]AATTAGGGATGCAATTACAAAGAGAAATTTG ATAGAGATGGAAGATGATT |
| mME15248 | [C/T] | CC | 3 | GTTTGGTATCTGTTGGGATCCATGATTCTGCAT [C/T]CTTACTTGTACTGGAACTTGGGAGTGTTTGGAA GTAGGCAGTTATTTCCC |
| mME17306 | [C/T] | CC | 4 | TAATGGTGAAAAACAAGATTGCTGACGATAAATT GGTACCGAATTATCAA[C/T]ACGAAACCAAACAA AAACTTGGCTAAGTTATGGGATTGGATAGGCATT CC |
| mME26059 | [A/T] | AA | 5 | ACAAAAAGTATAACACATCAATATACGTGGAAAC TTGTAAAGGGAGAAAA[A/T]CTACGATRGAGACT TTTCTTATTATTTTCTTATGAAACATGAAGATACA A |
| mME38084 | [A/G] | GG | 6 | GCCGTGTAGCGTCTCTCTCTAAAACAGACATT [A/G]CCATAAAATTTCAGAAAAAGAAACAAATTACG AACATAAAACCAAAGCAT |
| mME21974 | [A/C] | CC or AC | 7 | TTAGCGGCATGCAAATTCACTTTATCCAAAGGAT TGATTCCGATGGTCTT[A/C]GAGGCCAGATGCGAC ATTGGCGGCGBTTGGACRGAGACGCTRSACGGC |
| mME12777 | [C/T] | CC | 8 | TGCGGCGAAGAATCACACAGTCTGTAGGAGTACA ATAAGGATTCAAACAA[C/T]TTAGAAGGAAAATC AATAGAGCACGATTCTATGATACTCCTCAAAATT GA |
| mME15151 | [A/G] | GG | 9 | TTCTTTAACAGTTCTTGATTCGTGGGTCTCTTTCTT TTGTTGAATGTAGA[A/G]CGTTCTTCCTTGTCATTG TGGTAGAAAGAAAGTGAATTGAAACTTTAAAG |
| mME26139 | [A/C] | CC | 10 | ATTTAAATGCTAATAAATATCATATATACAGAAA CAAATGACTATGACGT[A/C]AAATTAGAGTAGAA ATTACCTGCTTGATACAATATAGGACAGAACTGT AA |
| mME48762 | [A/C] | CC | 11 | TTTCGAAGCATCGTTTACAAGCTGTTCCTGTGGTT GAGCTTTCCAATTCT[A/C]ACGTAATTGGTTTCATT ACACAGGTACTTACTACTGGTTTTAACAACCCC |
| mME25039 | [T/C] | CC | 12 | GAGGGAAGATAGTTAAACAACTCGGATAATGAG AGAGAAACCACAGAAAC[T/C]ATGGTTCTTTCATT GCATACTTAAACTARATCAATTTGGACCTTAGGTT T |
| mME40109 | [C/T] | TT | 13 | TTCATTGCAAGAGTCAACAGATAGCGGTGAAGAT GGACAAGCTARGAAGC[T/C]TAAAGGTGGCTCTA GGCTTACTTCTGATGCAGCCAATATTGATATCATT C |

Three markers were population specific, as shown in Table 1-B:

| Marker | SNP | Resistance genotype | SEQ ID | Sequence comprising SNP |
|---|---|---|---|---|
| mME17011 | [C/T] | TT | 66 | TGTCTCATTGAATTAACAATCTGATACGTTGTCGA ACTGTCCAATCCTGT[C/T]GATATCTCGTCCATGA ACAGAGCTCTCGCTGGTCCAACCAACATCTCCCC |
| mME22724 | [A/G] | AA | 67 | AATTTAAATTTTTTGTCAAATATATACATCAATTT ACACCCTG[A/G]ACGTAGATTTCCTAGCTAATCAA TCCAGACCATTTATCAAATAATCTATA |
| mME21134 | [C/T] | TT | 68 | ATTTTCCACAACAACAAATAAACCTAATAATGAA CACAATCGAATTCAGG[C/T]ACAGAACAAAGGCC ACGATCGGAGTTAAAAAAA |

From the analysis of markers spanning Wf_11.1 QTL interval on large (1,400 individuals each) $F_2$ populations of both crosses recombinants were selected. Phenotype data from replicated trial of $F_3$ families of these recombinants were matched with marker data of their respective $F_2$ progenitors. Field evaluation conducted in Spain of the two $F_4$ families obtained from two $F_3$ recombinants carrying Wf_11.1 QTL showed that the two $F_4$ families displayed significant higher resistance levels compared to their susceptible parents (Table 2 and FIG. 2) as determined by ANOVA (P<0.0001) both in the average number of adult white fly and average number of nymphs per 1.5 cm diameter leaf disc.

TABLE 2

Mean number of adult white fly and $3^{rd}$ instar nymphs in the 2013 field evaluation in Spain

| Genotype | Description | Ave. Nymph Count[x] | Ave. Adult Count[y] |
|---|---|---|---|
| NCIMB 41966 | Resistant Parent | 1.21a[z] | 2.39a[z] |
| NCIMB 41965 | Resistant Parent | 0.66a | 7.20a |
| NCIMB 42221 | $F_4$ Recombinant* | 1.32a | 9.85a |
| NCIMB 42220 | $F_4$ Recombinant* | 2.91ab | 8.90a |
| (990631-2)-Q-1-K | Susceptible Parent | 4.41b | 25.21b |
| (MA 17115)-Q-1-4 | Susceptible Parent | 7.01bc | 20.80b |

[x] Average number of third instar white fly nymphs per 1.5 cm diameter leaf disc
[y] Average number of adult whiteflies per leaf per plant
[z] Means were separated by LSD; means followed by the same letter are not significantly different at P < 0.05
*NCIMB4220 is progeny from the cross (990631-2)-Q-1-K (Wf susceptible) x NCIMB 41966 (Wf resistant); NCIMB 42221 is progeny from the cross (MA 17115)-Q-1-4 (Wf susceptible) x NCIMB 41965 (Wf resistant).

The above results show that the wild accessions NCIMB 41966 and NCIMB 41965 comprise a QTL for whitefly resistance on chromosome 11 and that an introgression fragment comprising this QTL was transferred into two recombinant cultivated melon lines. These cultivated melon lines show very good field resistance against whitefly.

Example 2—SNP Assays (KASP Assay) or "Whitefly Marker Assay"

In order to screen plants for the presence of one or more of the above molecular markers, linked to the introgression fragment conferring whitefly resistance, a KASP-assay (a SNP genotyping assay or KBioscience Allele-Specific PCR genotyping-assay) was developed for thirteen (13) SNP markers as detailed in Table 3 and 4 below.

Based on the genomic sequences comprising the SNP (see Table 3 below and Sequence listing), for each SNP marker two allele-specific forward primers (i.e. detecting either the nucleotide of the susceptible or resistant parent at the SNP locus) and one common reverse primer (underlined and in italics) were developed, indicated in Table 3 and 4 (all sequences are given in 5' to 3' direction).

TABLE 3

| marker | SNP | SEQ ID | |
|---|---|---|---|
| mME12777 | [C/T] | 14 | CATCTTACAAAATGTATCAGAGGCATTTCTAAACTTTTTTAAATGAGCAAAAGTCTTGAAAAGC AGATCAAAAACATGCGGCGAAGAATCACACAGTC*TGTAGGAGTACAATAAGGATTCAAACAA* [C/T]TTAGAAGGAAA*ATCAATAGAGCACGATTCTATGATACTCCT*CAAAATTGATTCTGCAKGTACG CA |
| mME15151 | [A/G] | 15 | TTTTTTTTCTCTTCTTTAACAGTTCTTGAT*TCGTGGGTCTCTTTCTTTTGTTGAATGT*AGA[A/G]CGT TCTTCCTTGTCATTGTGGTAGAAAGAAAGTGAATTGAACTTTAAAGCTAGTTGTTTAATTGCT CTGTTCTGCCAAATGAGACCTTGTTTCTTGCTTTGGAATTGTTTATGAATGCCGAAACTGWTAT CGTAAGAATTGGTTTTYAATGTCAAGAATCTATTTGGCATGTTTCGGTTATGCTTTTCTTGAATT TTCTAGAAGTTTTCCTCTTATATGAATTCTTGTAAACAATTTTGGCTTTGGGAGTTATAATGCTG |

TABLE 3-continued

| marker | SNP | SEQ ID | |
|---|---|---|---|
| | | | AAGGATATTCTCCCTTTGTCTGTCTCTTCTTGTCACTCTGCTCAAAAGCAATATGATTATGAACT<br>TTTACCTTTAGTTCCATGGCTGTAATCGTAATGCTTTGGTTTGAATTGAACTTCAAGTCATGATA<br>TATTGGATTAGCTTTGAAATATTTGATGGTTGTATTTGTGGCATCCAGCATGTCTCAATATGGTA<br>AAGAAGGTTAGAGTCATTGAGTAACCTTTCCATTTTTTGTTTTTAGTTTTGATAAATATGTCTAT<br>TTGGAAAGTATTCGTTGTTTGCCATATCTTGATGTTTCTAATAACTGTACTCCAATTTGGAAATC<br>AAAACAAAATACTTTTCTTGTTTTGTTATGTCAATGTGTAACAATCCAAAGTTAGTATCAAGAG<br>AATCATAAGCAACAATAAAAATGAGGAAGATATGAAATGAGCCTAATTTATCATCAGTCGA<br>AGTACTGAAGTTGTGTGTATTTCTTCAGTTGTATAGATGGGTTGTTGCTAGAACCACAAAGCTT<br>TTCTTGTTTCCTTTGCACTCTCAGTTGCCTGAGAAAACCCGAGAGGATATCATAGTACTAAATG<br>TAGGTTCTATAATATGACGATAATCATTTGGTTTATGTTCTGTTACATTACTGGTTACATTTAAT<br>AAAACTCCAGGACGATATAGTATTTGTTGGATATATTTGCATACCTAGCTATATATTATAAGAT<br>GCAGATAATTCTTTCAGCTATAATTGACTTTRTTTCTCTTGTGATTTTAAGGATTTGCAACAACA<br>GCAACAATATGAACGGGGAGCTGCCCTCAATGAGATCGAACACAGCCGCAAGATCCTACTTGA<br>CAAGCTCAAGGATTACAAAGGAGAGTATTTGGAAGTGGTAAAGGAAGCTTCTGCCTTCGCTGG<br>GGAGGCAGTAAAGAACAACCATGACCTCATGCTTCCYCCATATCCAAGTCGCTCCMCATATCC<br>TCTTCACCTAGACAATGACCATTTATCACCATTCGTRTCTGCTCGCAAATCTGCCCGTAATGGG<br>GTAACCTTGAGCTACATGACAAATGATGCCAAAAGAGAGTCAAGCGAGTCACTAAGTACCAGC<br>AAAGAAGCGAGCACGAAAAACACAAGGAATGGATTAGGTTCACTCATAGCTGCAKGTACGCC<br>GTCTAGACTG |
| mME15248 | [C/T] | 16 | GTTTGG*TATCTGTTGGGATCCATGATTCTGCAT*[C/T]CTTACTTGTACTGGAACTTGGGAGTGTTTG<br>GAAGTAGGCAGTTATTTCCCATTTGCAATCTGTTATAAGAAGGTAAAATTATAAAAGTTCTTTC<br>AATTTT |
| mME17011 | [C/T] | 17 | GCTACACGGCTGCAACAAGAAAATGAGAGGGCCAATTACTTAGATTTTTCAGTTGTTAGTTTTG<br>AACATTTCGTTTGCATAAATCAAAAAGTCTCTTACATGTCTCCCACTTATGGCCAAGAAACTCAT<br>TCACAGCTATTCCATTTTGTGCATACATCATTGGAGAGGTCCAGTAGCCCCAAATCCACCAAGG<br>ATGCACATCATCTAAACATAAAGAGAAGTTCTCATTTAAGTAATTTTTCTTATGTAATGGTATT<br>GAAAACACATAGGTCACTTGAATCAAACCTCGAGCTAAGACAAATCCACCCAAAACAAGAACT<br>GTAAGTAAAGCAAATGATCCAAATGTATTTGCAACGATGATATTCCGTCCCAATGCTCCAATCA<br>AACGGAACAGCGCAGATGCCATTTGGTTCACACACAGGAGCAGGAGAAAATGTTTGAAGAATC<br>TGCAAGTCCATCATACGACCTAATGTTATCAAGAAGGTAAAATAATCAAATTGGTAGTTCAGT<br>GTTAGTGTTCTTCATTTTCTTGTACCTTCCGGCGTTTGGATCGAATCCAACGACATAGTAAGTCA<br>TTACCACCCAAATTCCAACTTCGACAAAAGTAATAGGGATCTTAAGGATCCATGTGGGTATAG<br>AATATGCCCAAGGGGAAAGAAGAGGAAGTCCCTTTGCTTGTGAACACAGGAAGTTTCAAGA<br>TTGTCAAAGCAAGCTCAGAGAAACCATTGAACATGATTATGATAATCGCAAAGAACAATGCTC<br>CCATGTAAACCGATCCATCATCTACTGTCCTCCGGCGCATCTCGGTTCGGAAAACAAGGTCAT<br>TGTCACAAAAGCCATCAGAATGAGCTGAAAAATGAAGAAACATAGTAGTGTCAAACATGAGCT<br>ATCGGAGAGTGAATAAAGATATGAACTACGGAACTAAAACTCACTTGAGTCAACTTGAAAATG<br>TACACAAATGAGTTTCTCTTCATGAGTAAAAGCTCCCTTGAAATGCAAGCTTTCAACAGTTCCT<br>TCTTGCTAGCACCCATACTTCTCGGTTGTTAAAGCAGCAGGGTGGCTTTTAGAYTTGTCAAATGG<br>AGTGGCAAGCTCATCACCTAGCTTCTTCCCCACATGAAATGATTGAAAGGCTTCAGAAAACTCC<br>TCCACACTGACAAATCTATAAACCTCATCTCTCTTAGTCCAATATTGTTCTTGATCTTTCCTTGA<br>AGTGACCTATAAAACAGTTTCCATCAGCTCAAACAAAATGGATGAAASAAATAGCAGAAAAGA<br>ACACATTATGAAAATGGGGAAAGTTAAAAGGCCAAACGAGCTTACTCTTGTAAGAAGTCAGC<br>TACTCCTTTCCTCTGAGGGCAAGTGAAGCCCATATGTTGGAAGAACTCGAGCACGTTTTCACGT<br>GGACCTTGATACACAACTTGTCCATCTGATATCGAATTTATGTCATCAAACAATTCATAAGTTT<br>CAGGGGMCGGWTGAAGAAGAGAGATCAGAGCAGTTCCATTCAGAATATGAATGGACTGTCTC<br>ATTGGAATTAACAATCTGATACGTTGTCGAACTGTCCAATCCTGT[C/T]GA*TATCTCGTCCATGAAC<br>AGAGCTCTC*GCTGGTCCAACCAACATCTCCCCAGTCGTCACCCTCTTCTTTTGCCCACCGGAGAT<br>CCCTCGAAACATTTCATCTCCTACCATTGTGTCAGCACRGATTTCAAGTCCTAGAATCTGCATA<br>AACAATCAAAAAACATTATAAGACCATATACTATTAGTTTMTTTGCTGCTTAGTTTTTTTGCT<br>GCTTAGTTATTATTACAAAAAGTTTTCACCTTTAGTACATAATCTGTCACTACATTGGTTTCTTG<br>TCCTCCTAAAGCTGCAKGTACGCA |
| mME17306 | [C/T] | 18 | TCCTAAGGTAATCTGAGAGACGTTCAATTTCAGACTGTTCAAAGGATCCCTAATGGTGAAAAA<br>CAAGATTGC*TGACGATAAATTGGTACCGAATTATCAA*[C/T]ACGAAACCAAACAA*AAACTTGGC<br>TAAGTTATGGGATTGGATAGG*CATTCCGCTTTTGACTTTTCTATCATTGGATTGAACTCGAAGGAA<br>ATGCCTCGATC |
| mME17490 | [A/G] | 19 | GCATTTTACAGCATAGAAAAACTATGGTCGGGC[A/G]*AATTAGGGATGCAAATTACAAAGAGAAAT<br>TTG*ATAGAGATGGAAGATGATTAGATTACCTGGATGAGAGTTAGGGCTCCTAGTACAAGAAAG<br>GTACATAAAATGAATGACGCCGTCTTAGCCCATTCGCCSKGTAGCTTCTCTATAGAGACGCTAC |
| mME20364 | [C/T] | 20 | GCGTACMTGCAGCGGATGTACTTTGAAGATCCATATCCATTATCATCAGATGATCGTAAGGGTT<br>GGTTACGCAAGGGTC*GACTTTCAATCTGTTTGAGAAAACAAG*[C/T]GGTTCT*TAGCTMTTGACCT<br>TTATGATAGGTGCC*TTGAGAAGGGCCCTCRTGGTCATTGGGCAAAAATAAATACCTTTGTTAGGT<br>TGATTTGGCGAAGAGCAAAAACTGCAAGTGCCTTGAAGAGAATTCCCGGACCCTCCTCTAGTG<br>AGAAAACTATACTTGTCTGAAAAGGAAGCGAGCATATTACATACAACAAYGTACTTATTCTAA<br>GCACCATATACATGAATGCAAAGAATTAGAAGGGAAGAGACTCTTTTCCTCCTAAAAAWACGA<br>AAGGCTAACCTTGAATGGCCTATCAATGCCTGGAATTATGGGTTTTCTCGCTAGCATTAGAAAT<br>CGAGTTACATTGTCAGAGTCATCCTAATAGAAGAAAGAAAATTGGTAATCGGTGCAGCATTA<br>GAATGTATGGGCTAGTAAATCATAATTAAATGCTTAAGTAAACACCTGAATATCTTCAGCAAGT<br>ATATTCAAGCCATATATGGACGCAGCCACSGAGCTAGCAACAGCTCCTGCATCTTTCAATTTGT<br>GAAAAGCAACATGCTGCACAATATCMAAGTCTCATCAACTATCATTCTGAACCAGCAATCAA<br>AATGATGAAAATTGGATGATACGAATATATAATCATCAATCATCAAAACTTCATATAAGCATT<br>GCTGATAAATAAGCATCAACAAAAATCTGATTTGCCTTCTCAGAATCACTATYGAGCCATIATA |

TABLE 3-continued

| marker | SNP | SEQ ID | |
|---|---|---|---|
| | | | ATAATAARAAATGACAAGTTTTCCTGTAGAATAGACCAAAAAATGACAAAATATCATAACAGT AACGGAGCAGCAATTGAACAGCCAAAGATAAAGTACCTTTGCAGCACCAGCAGTATCGTCCAC TGCTTCTCTCACCAATCCTAGCCCTGTCAATGTGTTTTCACACTGRGCMAGAGCCTGAACAAGA ATCATGTTAAGCCGKGTAGCGTCTCAGACTGCGTAC |
| mME21134 | [C/T] | 21 | TTCAAAAGTAGAAACAAGAGAATTCAACTTGTTTCATAAACATATTCCAGATTTTCCACAACAA CAAATAAAC*CTAATAATGAACACAATCGAATTCAGG*[C/T]ACAG*AACAAAGGCCACGATCGGAG TTAAAAAAA* |
| mME21974 | [A/C] | 22 | AGAGACGCTACMCGGAGTAAGCGGATTAGCGGCATGCAAATTCACT*TTATCCAAAGGATTGATT CCGATGGTCTT*[A/C]GAGGCCAGATGCGACATTGGCGGCGBTTGGACRGAGACGCTRSACGGC |
| mME22724 | [A/G] | 23 | AATTTAAATTTTTTGTCAAATATATACATCAATTTACACCCTG[A/G]ACG*TAGATTTCCTAGCTAAT CAATCCAGACC*ATTTATCAAATAATCTATATCTAATTTTACTAGATCCCATTCAAAATCAACTCA AAATTATCTAAATAAATTACTTTTCTTCAAAAAGTCCCCAAGTAGCAGAACCAATAGAAAAC GGGAAATTTAATGAAGTCGTAAGTTCAACTTTAACAATTTTTAAAACAAAATTCTAATAGATTG TTTAAACTGATTTACTTATTAATTTGAGATTTTGTGGATACAAGCCGTAAAAGTTAAAAAAGG GGTATAAATGAACTTATATTATTCAAAATTTATCAAATTTATTCATAGGAAATGAAGCACCAAG GAATACCAGAAAATAAWTGACA |
| mME26059 | [A/T] | 24 | CGCTACMCGGTTCAGGGCCAAGAATATAAGCCCAAATTGCATTGTAATCAACAGAGCTMCTAT TTTTAATCATTGTGGACYCAACTTGTGTTAGGTGTGTATTAAGCAATGCCTTGTCAAGCACATTT GAAATGACATGCAACCCAAGGACACGTTGACCTGGTATCTGACACCAACGAGAAGCTAGAGTG AAAATTATTGAAAGAGACAAAAAGTATAACACATCAATATACGTGGAAACTTGTAAAGGGAG AAAA[A/T]CTACGATRGAGACTTTTCTTATTAT*TTTCTTATGAAACATGAAGATACAAAGGCG*AAGA ATTAACAGGCAACAAAAGCTTTAACAAAAACGGAAAGAAACAGTAGGTAAAATAATTTACAT AAATACCCTTGAGCTTTCAACATACAAGAAGCCCATAAATTCTGACAGAAGGTTTAAAGAGTT CAAAATAACAAACTTCTAGAAGATTTGAAATAAATGAAAAAAGAGCTATTTCATAACGAATAA GAAAAATAAGGGGCCAAAGTGGAAAAAAACYAACAGTATTTTATGGTTGAAAAAAATTGTC ACTACAATGAAGCAACTA |
| mME38084 | [A/G] | 25 | GCCG*TGTAGCGTCTCTCTCTAAAACAGACATT*[A/G]CCATAAAATTTCAGAAAAAGAAACAAATTA *C*GAACATAAAACCAAAGCATTAAGAGTAGAATCAAATAAATGAAGAATCCAATCACAGAAAC AGCAGGAA |
| mME48762 | [A/C] | 26 | TTATTTTCCTGTTGGAATGAGGGATACACTTTTTCATGTTCTTCTTATGTTTCGAAGCATCGTTT ACAAG*CTGTTCCTGTGGTTGAGCTTTCC*AATTCT[A/C]ACGTAATTGGTTTCATTACACAGGTACTT ACTACTGGTTTTAACAACCCCGTCGATTACTTTTGACTAATCTTATGGGACAACACCTTTTAACA TTTAGG |

TABLE 4

| marker | SNP | Primer-allele FAM (dye) | Primer-allele VIC (dye) | Probe FAM | Probe VIC | Primer Common (in Table 3 the annealing sequence for this primer is underlined and in italics) |
|---|---|---|---|---|---|---|
| mME12777 | [C/T] | GAAGGTGACCAAGTT CATGCTGTAGGAGTAC AATAAGGATTCAAAC AAC (SEQ ID NO: 27) | GAAGGTCGGAGTCAACGG ATTGTAGGAGTACAATAAG GATTCAAACAAT (SEQ ID NO: 28) | C | T | *GGAGTATCATAGAATCGTGCTCT ATTGAT* (SEQ ID NO: 29) |
| mME15151 | [A/G] | GAAGGTGACCAAGTT CATGCTACCACAATGA CAAGGAAGAACGT (SEQ ID NO: 30) | GAAGGTCGGAGTCAACGG ATTACCACAATGACAAGGA AGAACGC (SEQ ID NO: 31) | T | C | *TCGTGGGTCTCTTTCTTTTGTTGA ATGTA* (SEQ ID NO: 32) |
| mME15248 | [C/T] | GAAGGTGACCAAGTT CATGCTCCCAAGTTCC AGTACAAGTAAGG (SEQ ID NO: 33) | GAAGGTCGGAGTCAACGG ATTCTCCCAAGTTCCAGTA CAAGTAAGA (SEQ ID NO: 34) | G | A | *TATCTGTTGGGATCCATGATTCT GCAT* (SEQ ID NO: 35) |
| mME17011 | [C/T] | GAAGGTGACCAAGTT CATGCTTGTCGAACTG TCCAATCCTGTC (SEQ ID NO: 36) | GAAGGTCGGAGTCAACGG ATTGTTGTCGAACTGTCCA ATCCTGTT (SEQ ID NO: 37) | C | T | *GAGAGCTCTGTTCATGGACGAGA TA* (SEQ ID NO: 38) |
| mME17306 | [C/T] | GAAGGTGACCAAGTT CATGCTGACGATAAAT TGGTACCGAATTATCA (SEQ ID NO: 39) | GAAGGTCGGAGTCAACGG ATTGACGATAAATTGGTAC CGAATTATCAAT (SEQ ID NO: 40) | C | T | *CTATCCAATCCCATAACTTAGCCA AGTTT* (SEQ ID NO: 41) |

TABLE 4-continued

| marker | SNP | Primer-allele FAM (dye) | Primer-allele VIC (dye) | Probe FAM | Probe VIC | Primer Common (in Table 3 the annealing sequence for this primer is underlined and in italics) |
|---|---|---|---|---|---|---|
| mME17490 | [A/G] | GAAGGTGACCAAGTT CATGCTAGCATAGAA AAACTATGGTCGGGC (SEQ ID NO: 42) | GAAGGTCGGAGTCAACGG ATTCATAGAAAAACTATGG TCGGGCG (SEQ ID NO: 43) | A | G | *CAAATTTCTCTTTGTAATTGCATC CCTAAT* (SEQ ID NO: 44) |
| mME20364 | [C/T] | GAAGGTGACCAAGTT CATGCTGACTTTCAAT CTGTTTGAGAAAACAA (SEQ ID NO: 45) | GAAGGTCGGAGTCAACGG ATTCGACTTTCAATCTGTTT GAGAAAACAAGT (SEQ ID NO: 46) | C | T | *GGCACCTATCATAAAGGTCAAKA GCTA* (SEQ ID NO: 47) |
| mME21134 | [C/T] | GAAGGTGACCAAGTT CATGCTAATAATGAAC ACAATCGAATTCAGGC (SEQ ID NO: 48) | GAAGGTCGGAGTCAACGG ATTCCTAATAATGAACACA ATCGAATTCAGGT (SEQ ID NO: 49) | C | T | *TTTTTTAACTCCGATCGTGGCCTT TGTT* (SEQ ID NO: 50) |
| mME21974 | [A/C] | GAAGGTGACCAAGTT CATGCTCCAATGTCGC ATCTGGCCTCT (SEQ ID NO: 51) | GAAGGTCGGAGTCAACGG ATTCCAATGTCGCATCTGG CCTCG (SEQ ID NO: 52) | T | G | *TTATCCAAAGGATTGATTCCGAT GGTCTT* (SEQ ID NO: 53) |
| mME22724 | [A/G] | GAAGGTGACCAAGTT CATGCTGTCAAATATA TACATCAATTTACACC CTGA (SEQ ID NO: 54) | GAAGGTCGGAGTCAACGG ATTCAAATATATACATCAA TTTACACCCTGG (SEQ ID NO: 55) | A | G | *TGGTCTGGATTGATTAGCTAGGA AATCTA* (SEQ ID NO: 56) |
| mME22724 | [A/T] | GAAGGTGACCAAGTT CATGCTACGTGGAAAC TTGTAAAGGGAGAAA AA (SEQ ID NO: 57) | GAAGGTCGGAGTCAACGG ATTACGTGGAAACTTGTAA AGGGAGAAAAT (SEQ ID NO: 58) | A | T | *CGCCTTTGTATCTTCATGTTTCAT AAGAAA* (SEQ ID NO: 59) |
| mME38084 | [A/G] | GAAGGTGACCAAGTT CATGCTCGTAATTTGT TTCTTTTTCTGAAATTT TATGGT (SEQ ID NO: 60) | GAAGGTCGGAGTCAACGG ATTGTAATTTGTTTCTTTTT CTGAAATTTTATGGC (SEQ ID NO: 61) | A | C | *TGTAGCGTCTCTCTCTAAAACAG ACATT* (SEQ ID NO: 62) |
| mME48762 | [A/C] | GAAGGTGACCAAGTT CATGCTGTACCTGTGT AATGAAACCAATTAC GTT (SEQ ID NO: 63) | GAAGGTCGGAGTCAACGG ATTACCTGTGTAATGAAAC CAATTACGTG (SEQ ID NO: 64) | T | G | *CTGTTCCTGTGGTTGAGCTTTCC AA* (SEQ ID NO: 65) |

Using the above primers, KASP-assays can be carried out according to standard protocols developed by KBioscience. co.uk (see www.kbioscience.co.uk), in order to detect the presence of either the resistant or susceptible SNP-genotype in homozygous or heterozygous form in plant DNA derived from melon cells or tissues. If the genotype at a given SNP is homozygous, only one fluorescent signal will be detected. If the genotype of the plant at a given SNP is heterozygous, a mixed fluorescent signal will be detected.

For any of the other SNP markers similar SNP-genotyping assays can be developed in order to detect the SNP-genotype.

The invention claimed is:

1. A non-wild, cultivated *Cucumis melo* plant, or part thereof, comprising resistance against whitefly, wherein said resistance is conferred by an introgression fragment on chromosome 11 in homozygous or heterozygous form and wherein said introgression fragment is from a wild plant of the species *Cucumis melo*, a representative sample of seeds has been deposited under accession number NCIMB 41965 and NCIMB 41966, and wherein said introgression fragment comprises at least one of the following Single Nucleotide Polymorphism (SNP) markers:

a) the CC genotype or CT genotype for the SNP marker mME20364 in SEQ ID NO: 1;
    b) the AA genotype or AG genotype for the SNP marker mME17490 in SEQ ID NO: 2;
    c) the CC genotype or CT genotype for the SNP marker mME15248 in SEQ ID NO: 3;
    d) the CC genotype or CT genotype for SNP marker mME17306 in SEQ ID NO: 4;
    e) the AA genotype or AT genotype for SNP marker mME26059 in SEQ ID NO: 5;
    f) the GG genotype or GA genotype for SNP marker mME38084 in SEQ ID NO: 6;
    g) the CC genotype or AC genotype for SNP marker mME21974 in SEQ ID NO: 7;
    h) the CC genotype or CT genotype for SNP marker mME12777 in SEQ ID NO: 8;
    i) the GG genotype or GA genotype for SNP marker mME15151 in SEQ ID NO: 9;
    j) the CC genotype or CA genotype for SNP marker mME26139 in SEQ ID NO: 10;
    k) the CC genotype or CA genotype for SNP marker mME48762 in SEQ ID NO: 11;
    l) the CC genotype or CT genotype for SNP marker mME25039 in SEQ ID NO: 12; and/or
    m) the TT genotype or TC genotype for SNP marker mME40109 in SEQ ID NO: 13.

2. The plant according to claim 1, wherein said introgression fragment comprises one or more of the following SNP markers:

i) the CC genotype or CT genotype for the SNP marker mME15248 in SEQ ID NO: 3;
    ii) the CC genotype or CT genotype for SNP marker mME17306 in SEQ ID NO: 4;
    iii) the AA genotype or AT genotype for SNP marker mME26059 in SEQ ID NO: 5;
    iv) the GG genotype or GA genotype for SNP marker mME38084 in SEQ ID NO: 6;
    v) the CC or AC genotype for SNP marker mME21974 in SEQ ID NO: 7; and/or
    vi) the CC genotype or CT genotype for SNP marker mME12777 in SEQ ID NO: 8.

3. The plant according to claim 1, wherein said introgression fragment is obtainable from seeds of which a representative sample has been deposited under NCIMB 42220 or NCIMB 42221.

4. The plant according to claim 1, wherein said plant is an F1 hybrid.

5. The plant according to claim 1, wherein said introgression fragment is equal to or less than 20 Mb in size.

6. The plant according to claim 1, wherein the average number of adult whiteflies and/or the average number of third instar nymphs found on the plant is 60%, or less, of the average number found on a whitefly susceptible variety when grown under the same conditions.

7. Seeds from which a plant according to claim 1 can be grown.

8. A melon fruit harvested from a plant according to claim 1, wherein said fruit cells comprise said introgression fragment in their genomic DNA.

9. A plant cell, tissue or plant part of a plant or of a seed according to claim 1, comprising at least one recombinant chromosome 11, wherein said recombinant chromosome 11 comprises an introgression fragment from a wild *C. melo* plant, a representative sample of seeds has been deposited under accession number NCIMB 41965 and NCIMB 41966, and wherein said introgression fragment comprises an allele conferring whitefly resistance.

10. A method for producing a *C. melo* plant comprising an introgression fragment on chromosome 11, wherein said introgression fragment comprises a whitefly resistance allele, comprising the steps of:
- a) crossing a first melon plant being susceptible to whitefly with a second wild melon plant being resistant to whitefly, a representative sample of seeds of said second melon plant has been deposited under accession number NCIMB 41965 and NCIMB 41966,
- b) backcrossing an F1, F2 or further selfing plant to the first melon plant to produce a backcross population, or selfing an F1 plant one or more times to produce an F2, F3 or further selfing population,
- c) optionally selfing the backcross population one or more times,
- d) identifying an F2, F3, or further selfing, or backcross plant which comprises
  - i) the CC or CT genotype for the SNP marker mME15248 in SEQ ID NO: 3; and/or
  - ii) the CC or CT genotype for SNP marker mME17306 in SEQ ID NO: 4; and/or
  - iii) the AA or AT genotype for SNP marker mME26059 in SEQ ID NO: 5; and/or
  - iv) the GG or GA genotype for SNP marker mME38084 in SEQ ID NO: 6; and/or
  - v) the CC or CA genotype for SNP marker mME21974 in SEQ ID NO: 7; and/or
  - vi) the CC or CT genotype for SNP marker mME12777 in SEQ ID NO: 8.

11. A method for identifying a *C. melo* plant comprising an introgression fragment on chromosome 11, wherein said introgression fragment comprises a whitefly resistance allele, comprising:
- a) screening a population of recombinant *C. melo* plants using a molecular marker assay which detects at least one SNP marker of: mME15248, mME17306, mME26059, mME38084, mME21974, mME12777; and
- b) identifying and/or selecting a plant comprising
  - i) the CC or CT genotype for the SNP marker mME15248 in SEQ ID NO: 3; and/or
  - ii) the CC or CT genotype for SNP marker mME17306 in SEQ ID NO: 4; and/or
  - iii) the AA or AT genotype for SNP marker mME26059 in SEQ ID NO: 5; and/or
  - iv) the GG or GA genotype for SNP marker mME38084 in SEQ ID NO: 6; and/or
  - v) the CC or CA genotype for SNP marker mME21974 in SEQ ID NO: 7; and/or
  - vi) the CC or CT genotype for SNP marker mME12777 in SEQ ID NO: 8.

12. A method of producing *C. melo* F1 hybrid seeds comprising a whitefly resistance phenotype comprising:
- a) crossing a first inbred melon plant comprising at least two recombinant chromosomes 11 having an introgression fragment comprising an allele conferring whitefly resistance with a second inbred melon plant with or without recombinant chromosome 11 having an introgression fragment comprising an allele conferring whitefly resistance, and
- b) collecting F1 hybrid seeds from said cross, wherein said introgression fragment is from a wild plant of the species *Cucumis melo*, a representative sample of seeds has been deposited under accession number NCIMB 41965 and NCIMB 41966, and wherein said introgression fragment comprises at least one of the following Single Nucleotide Polymorphism (SNP) markers:
- a) the CC genotype or CT genotype for the SNP marker mME20364 in SEQ ID NO: 1;
- b) the AA genotype or AG genotype for the SNP marker mME17490 in SEQ ID NO: 2;
- c) the CC genotype or CT genotype for the SNP marker mME15248 in SEQ ID NO: 3;
- d) the CC genotype or CT genotype for SNP marker mME17306 in SEQ ID NO: 4;
- e) the AA genotype or AT genotype for SNP marker mME26059 in SEQ ID NO: 5;
- f) the GG genotype or GA genotype for SNP marker mME38084 in SEQ ID NO: 6;
- g) the CC genotype or AC genotype for SNP marker mME21974 in SEQ ID NO: 7;
- h) the CC genotype or CT genotype for SNP marker mME12777 in SEQ ID NO: 8;
- i) the GG genotype or GA genotype for SNP marker mME15151 in SEQ ID NO: 9;
- j) the CC genotype or CA genotype for SNP marker mME26139 in SEQ ID NO: 10;
- k) the CC genotype or CA genotype for SNP marker mME48762 in SEQ ID NO: 11;
- l) the CC genotype or CT genotype for SNP marker mME25039 in SEQ ID NO: 12; and/or
- m) the TT genotype or TC genotype for SNP marker mME40109 in SEQ ID NO: 13.

13. A *C. melo* F1 hybrid melon plant produced by the method of claim 12, which plant comprises resistance against whitefly, wherein said resistance is conferred by an introgression fragment on chromosome 11 in homozygous or heterozygous form.

14. A method of producing *C. melo* F1 hybrid plants comprising a whitefly resistance phenotype comprising, growing the F1 hybrid seeds of claim 12.

15. The plant according to claim 2, wherein said introgression fragment comprises the AA genotype or AT genotype for SNP marker mME26059 in SEQ ID NO: 5, and one or more of the CC genotype or CT genotype for the SNP marker mME15248 in SEQ ID NO: 3; the CC genotype or CT genotype for SNP marker mME17306 in SEQ ID NO: 4; the GG genotype or GA genotype for SNP marker mME38084 in SEQ ID NO: 6; or the CC or AC genotype for SNP marker mME21974 in SEQ ID NO: 7.

16. The plant according to claim 2, wherein said introgression fragment comprises the CC genotype or CT genotype for SNP marker mME17306 in SEQ ID NO: 4, and the AA genotype or AT genotype for SNP marker mME26059 in SEQ ID NO: 5.

17. The plant according to claim 2, wherein said introgression fragment comprises the AA genotype or AT genotype for SNP marker mME26059 in SEQ ID NO: 5, and the GG genotype or GA genotype for SNP marker mME38084 in SEQ ID NO: 6.

18. The plant according to claim 2, wherein said introgression fragment comprises the CC genotype or CT genotype for SNP marker mME17306 in SEQ ID NO: 4, the AA genotype or AT genotype for SNP marker mME26059 in SEQ ID NO: 5, and the GG genotype or GA genotype for SNP marker mME38084 in SEQ ID NO: 6.

19. The plant according to claim 2, wherein said introgression fragment comprises the CC genotype or CT genotype for the SNP marker mME15248 in SEQ ID NO: 3, the CC genotype or CT genotype for SNP marker mME17306 in SEQ ID NO: 4, the AA genotype or AT genotype for SNP marker mME26059 in SEQ ID NO: 5, the GG genotype or GA genotype for SNP marker mME38084 in SEQ ID NO: 6, and the CC or AC genotype for SNP marker mME21974 in SEQ ID NO: 7.

20. The plant according to claim 1, wherein said introgression fragment is equal to or less than 10 Mb in size.

\* \* \* \* \*